(12) United States Patent
Dwivedi et al.

(10) Patent No.: US 11,871,946 B2
(45) Date of Patent: Jan. 16, 2024

(54) CLOT RETRIEVAL DEVICE FOR REMOVING CLOT FROM A BLOOD VESSEL

(71) Applicant: Neuravi Limited, Galway (IE)

(72) Inventors: Anushree Dwivedi, Galway (IE); Patrick Connolly, Galway (IE)

(73) Assignee: NEURAVI LIMITED, Galway (IE)

( * ) Notice: Subject to any disclaimer, the term of this patent is extended or adjusted under 35 U.S.C. 154(b) by 0 days.

(21) Appl. No.: 16/852,099

(22) Filed: Apr. 17, 2020

(65) Prior Publication Data

US 2021/0322037 A1 Oct. 21, 2021

(51) Int. Cl.
*A61B 17/221* (2006.01)
*A61B 17/22* (2006.01)
*A61B 17/00* (2006.01)

(52) U.S. Cl.
CPC .. *A61B 17/221* (2013.01); *A61B 2017/00867* (2013.01); *A61B 2017/2215* (2013.01); *A61B 2017/22079* (2013.01)

(58) Field of Classification Search
CPC ............ A61B 17/22031; A61B 17/221; A61B 2017/22034; A61B 2017/22035; A61B 2017/22079; A61B 2017/2212; A61B 2017/2215; A61B 2017/2217; A61B 2017/00867; A61F 2/01; A61F 2/0103; A61F 2/0105; A61F 2/0108; A61F 2/012; A61F 2/013; A61F 2/014
USPC ....................................................... 606/200
See application file for complete search history.

(56) References Cited

U.S. PATENT DOCUMENTS

| 2,828,147 A | 3/1958 | Peiffer |
| 3,361,460 A | 1/1968 | Gerhart |
| 4,455,717 A | 6/1984 | Gray |
| 4,611,594 A | 9/1986 | Grayhack et al. |
| 4,612,931 A | 9/1986 | Dormia |
| 4,643,184 A | 2/1987 | Mobin-Uddin |
| 4,727,873 A | 3/1988 | Mobin-Uddin |

(Continued)

FOREIGN PATENT DOCUMENTS

| CN | 101172051 A | 5/2008 |
| CN | 102307613 A | 1/2012 |

(Continued)

OTHER PUBLICATIONS

US 6,348,062 B1, 02/2002, Hopkins et al. (withdrawn)

(Continued)

*Primary Examiner* — Kankindi Rwego
(74) *Attorney, Agent, or Firm* — Troutman Pepper Hamilton Sanders LLP

(57) ABSTRACT

A clot removal device including a first scaffolding section, a second scaffolding section distal of the first scaffolding section by a first hinged element including a pinching cell. The pinching cell has a collapsed state and an expanded state configured to pinch at least a portion of a clot. A third scaffolding section is distal of the second scaffolding section by a second hinged strut element including a pinching cell that has a collapsed state and an expanded state configured to pinch at least a portion of the clot. An outer diameter of the third scaffolding section is greater than an outer diameter of the second scaffolding section, which is greater than an outer diameter of the first scaffolding section.

17 Claims, 6 Drawing Sheets

(56) References Cited

U.S. PATENT DOCUMENTS

| | | |
|---|---|---|
| 4,793,348 A | 12/1988 | Palmaz |
| 4,873,978 A | 10/1989 | Ginsburg |
| 5,011,488 A | 4/1991 | Ginsburg |
| 5,084,065 A | 1/1992 | Weldon et al. |
| 5,092,839 A | 3/1992 | Kipperman |
| 5,100,423 A | 3/1992 | Fearnot |
| 5,102,415 A | 4/1992 | Guenther et al. |
| 5,108,419 A | 4/1992 | Reger et al. |
| 5,122,136 A | 6/1992 | Guglielmi et al. |
| 5,163,951 A | 11/1992 | Pinchuk et al. |
| 5,171,233 A | 12/1992 | Amplatz et al. |
| 5,171,259 A | 12/1992 | Inoue |
| 5,217,441 A | 6/1993 | Shichman |
| 5,234,437 A | 8/1993 | Sepetka |
| 5,236,447 A | 8/1993 | Kubo et al. |
| 5,330,482 A | 7/1994 | Gibbs et al. |
| 5,383,887 A | 1/1995 | Nadal |
| 5,387,219 A | 2/1995 | Rappe |
| 5,387,226 A | 2/1995 | Miraki |
| 5,449,372 A | 9/1995 | Schmaltz et al. |
| 5,499,985 A | 3/1996 | Hein et al. |
| 5,538,512 A | 7/1996 | Zenzon et al. |
| 5,538,515 A | 7/1996 | Kafry et al. |
| 5,549,626 A | 8/1996 | Miller et al. |
| 5,558,652 A | 9/1996 | Henke |
| 5,609,627 A | 3/1997 | Goicoechea et al. |
| 5,624,461 A | 4/1997 | Mariant |
| 5,639,277 A | 6/1997 | Mariant et al. |
| 5,639,278 A | 6/1997 | Dereume et al. |
| 5,645,558 A | 7/1997 | Horton |
| 5,653,605 A | 8/1997 | Woehl et al. |
| 5,658,296 A | 8/1997 | Bates et al. |
| 5,665,117 A | 9/1997 | Rhodes |
| 5,695,519 A | 12/1997 | Summers et al. |
| 5,709,704 A | 1/1998 | Nott et al. |
| 5,713,853 A | 2/1998 | Clark et al. |
| 5,769,871 A | 6/1998 | Mers Kelly et al. |
| 5,769,884 A | 6/1998 | Solovay |
| 5,779,686 A | 7/1998 | Sato et al. |
| 5,779,716 A | 7/1998 | Cano et al. |
| 5,800,519 A | 9/1998 | Sandock |
| 5,810,874 A | 9/1998 | Lefebvre |
| 5,814,064 A | 9/1998 | Daniel et al. |
| 5,827,304 A | 10/1998 | Hart |
| 5,853,422 A | 12/1998 | Huebsch et al. |
| 5,855,598 A | 1/1999 | Pinchuk |
| 5,893,869 A | 4/1999 | Barnhart et al. |
| 5,895,398 A | 4/1999 | Wensel et al. |
| 5,897,567 A | 4/1999 | Ressemann et al. |
| 5,904,698 A | 5/1999 | Thomas et al. |
| 5,911,702 A | 6/1999 | Romley et al. |
| 5,911,725 A | 6/1999 | Boury |
| 5,919,126 A | 7/1999 | Armini |
| 5,931,509 A | 8/1999 | Bartholomew |
| 5,935,139 A | 8/1999 | Bates |
| 5,947,995 A | 9/1999 | Samuels |
| 6,063,113 A | 5/2000 | Kavteladze et al. |
| 6,066,149 A | 5/2000 | Samson et al. |
| 6,066,158 A | 5/2000 | Engelson et al. |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates et al. |
| 6,099,559 A | 8/2000 | Nolting |
| 6,102,932 A | 8/2000 | Kurz |
| 6,106,548 A | 8/2000 | Roubin et al. |
| 6,129,739 A | 10/2000 | Khosravi |
| 6,143,022 A | 11/2000 | Shull et al. |
| 6,146,404 A | 11/2000 | Kim et al. |
| 6,156,064 A | 12/2000 | Chouinard |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,221,006 B1 | 4/2001 | Dubrul et al. |
| 6,221,096 B1 | 4/2001 | Aiba et al. |
| 6,231,597 B1 | 5/2001 | Deem et al. |
| 6,238,412 B1 | 5/2001 | Dubrul et al. |
| 6,245,012 B1 | 6/2001 | Kleshinski |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,267,777 B1 | 7/2001 | Bosma et al. |
| 6,290,710 B1 | 9/2001 | Cryer et al. |
| 6,312,444 B1 | 11/2001 | Barbut |
| 6,315,778 B1 | 11/2001 | Gambale et al. |
| 6,325,815 B1 | 12/2001 | Kusleika et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,346,116 B1 | 2/2002 | Brooks et al. |
| 6,348,056 B1 | 2/2002 | Bates et al. |
| 6,350,271 B1 | 2/2002 | Kurz et al. |
| 6,355,057 B1 | 3/2002 | DeMarais et al. |
| 6,361,545 B1 | 3/2002 | Macoviak et al. |
| 6,364,895 B1 | 4/2002 | Greenhalgh |
| 6,375,668 B1 | 4/2002 | Gifford et al. |
| 6,375,670 B1 | 4/2002 | Greenhalgh |
| 6,383,205 B1 | 5/2002 | Samson et al. |
| 6,383,206 B1 | 5/2002 | Gillick et al. |
| 6,391,037 B1 | 5/2002 | Greenhalgh |
| 6,402,771 B1 | 6/2002 | Palmer et al. |
| 6,416,541 B2 | 7/2002 | Denardo |
| 6,425,909 B1 | 7/2002 | Dieck et al. |
| 6,428,558 B1 | 8/2002 | Jones et al. |
| 6,432,122 B1 | 8/2002 | Gilson et al. |
| 6,436,112 B2 | 8/2002 | Wensel et al. |
| 6,458,139 B1 | 10/2002 | Palmer et al. |
| 6,485,497 B2 | 11/2002 | Wensel et al. |
| 6,485,501 B1 | 11/2002 | Green |
| 6,485,502 B2 | 11/2002 | Don Michael et al. |
| 6,488,701 B1 | 12/2002 | Nolting et al. |
| 6,511,492 B1 | 1/2003 | Rosenbluth et al. |
| 6,530,935 B2 | 3/2003 | Wensel et al. |
| 6,530,939 B1 | 3/2003 | Hopkins et al. |
| 6,540,768 B1 | 4/2003 | Diaz et al. |
| 6,544,279 B1 | 4/2003 | Hopkins et al. |
| 6,551,341 B2 | 4/2003 | Boylan et al. |
| 6,551,342 B1 | 4/2003 | Shen et al. |
| 6,575,996 B1 | 6/2003 | Denison et al. |
| 6,575,997 B1 | 6/2003 | Palmer et al. |
| 6,582,448 B1 | 6/2003 | Boyle et al. |
| 6,585,756 B1 | 7/2003 | Strecker |
| 6,589,265 B1 | 7/2003 | Palmer et al. |
| 6,592,607 B1 | 7/2003 | Palmer et al. |
| 6,592,614 B2 | 7/2003 | Lenker et al. |
| 6,592,616 B1 | 7/2003 | Stack et al. |
| 6,598,265 B2 | 7/2003 | Lee |
| 6,602,265 B2 | 8/2003 | Dubrul et al. |
| 6,602,271 B2 | 8/2003 | Adams et al. |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,632,241 B1 | 10/2003 | Hancock et al. |
| 6,638,245 B2 | 10/2003 | Miller et al. |
| 6,638,293 B1 | 10/2003 | Makower et al. |
| 6,641,590 B1 | 11/2003 | Palmer et al. |
| 6,656,218 B1 | 12/2003 | Denardo et al. |
| 6,660,021 B1 | 12/2003 | Palmer et al. |
| 6,663,650 B2 | 12/2003 | Sepetka et al. |
| 6,673,089 B1 | 1/2004 | Yassour et al. |
| 6,685,722 B1 | 2/2004 | Rosenbluth et al. |
| 6,692,504 B2 | 2/2004 | Kurz et al. |
| 6,692,508 B2 | 2/2004 | Wensel et al. |
| 6,692,509 B2 | 2/2004 | Wensel et al. |
| 6,695,858 B1 | 2/2004 | Dubrul et al. |
| 6,702,782 B2 | 3/2004 | Miller et al. |
| 6,702,834 B1 | 3/2004 | Boylan et al. |

(56) References Cited

U.S. PATENT DOCUMENTS

| | | |
|---|---|---|
| 6,709,465 B2 | 3/2004 | Mitchell et al. |
| 6,712,834 B2 | 3/2004 | Yassour et al. |
| 6,726,701 B2 | 4/2004 | Gilson et al. |
| 6,726,703 B2 | 4/2004 | Broome et al. |
| 6,730,104 B1 | 5/2004 | Sepetka et al. |
| 6,783,528 B2 | 8/2004 | Vincent-Prestigiacomo |
| 6,783,538 B2 | 8/2004 | McGuckin, Jr. et al. |
| 6,824,545 B2 | 11/2004 | Sepetka et al. |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer et al. |
| 6,913,618 B2 | 7/2005 | Denardo et al. |
| 6,939,361 B1 | 9/2005 | Kleshinski |
| 6,953,472 B2 | 10/2005 | Palmer et al. |
| 6,989,019 B2 | 1/2006 | Mazzocchi et al. |
| 6,989,021 B2 | 1/2006 | Bosma et al. |
| 6,994,718 B2 | 2/2006 | Groothuis et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,008,434 B2 | 3/2006 | Kurz et al. |
| 7,033,376 B2 | 4/2006 | Tsukernik |
| 7,041,116 B2 | 5/2006 | Goto et al. |
| 7,048,758 B2 | 5/2006 | Boyle et al. |
| 7,052,500 B2 | 5/2006 | Bashiri et al. |
| 7,058,456 B2 | 6/2006 | Pierce |
| 7,063,707 B2 | 6/2006 | Bose et al. |
| 7,083,633 B2 | 8/2006 | Morrill et al. |
| 7,083,822 B2 | 8/2006 | Brightbill |
| 7,094,249 B1 | 8/2006 | Broome et al. |
| 7,097,653 B2 | 8/2006 | Freudenthal et al. |
| 7,101,380 B2 | 9/2006 | Khachin et al. |
| 7,172,614 B2 | 2/2007 | Boyle et al. |
| 7,175,655 B1 | 2/2007 | Molaei |
| 7,179,273 B1 | 2/2007 | Palmer et al. |
| 7,185,922 B2 | 3/2007 | Takayanagi et al. |
| 7,220,271 B2 | 5/2007 | Clubb et al. |
| 7,226,464 B2 | 6/2007 | Garner et al. |
| 7,229,472 B2 | 6/2007 | DePalma et al. |
| 7,241,304 B2 | 7/2007 | Boyle et al. |
| 7,288,112 B2 | 10/2007 | Denardo et al. |
| 7,300,458 B2 | 11/2007 | Henkes et al. |
| 7,306,618 B2 | 12/2007 | Demond et al. |
| 7,314,483 B2 | 1/2008 | Andau et al. |
| 7,316,692 B2 | 1/2008 | Huffmaster |
| 7,323,001 B2 | 1/2008 | Clubb et al. |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins et al. |
| 7,425,215 B2 | 9/2008 | Boyle et al. |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka et al. |
| 7,556,636 B2 | 7/2009 | Mazzocchi et al. |
| 7,582,111 B2 | 9/2009 | Krolik et al. |
| 7,594,926 B2 | 9/2009 | Linder et al. |
| 7,604,649 B2 | 10/2009 | McGuckin, Jr. et al. |
| 7,604,650 B2 | 10/2009 | Bergheim |
| 7,609,649 B1 | 10/2009 | Bhandari et al. |
| 7,618,434 B2 | 11/2009 | Santra et al. |
| 7,662,165 B2 | 2/2010 | Gilson et al. |
| 7,670,356 B2 | 3/2010 | Mazzocchi et al. |
| 7,678,123 B2 | 3/2010 | Chanduszko |
| 7,691,121 B2 | 4/2010 | Rosenbluth et al. |
| 7,691,124 B2 | 4/2010 | Balgobin |
| 7,708,770 B2 | 5/2010 | Linder et al. |
| 7,717,929 B2 | 5/2010 | Fallman |
| 7,736,385 B2 | 6/2010 | Agnew |
| 7,749,246 B2 | 7/2010 | McGuckin, Jr. et al. |
| 7,758,606 B2 | 7/2010 | Streeter et al. |
| 7,758,611 B2 | 7/2010 | Kato |
| 7,766,934 B2 | 8/2010 | Pal et al. |
| 7,771,452 B2 | 8/2010 | Pal et al. |
| 7,780,694 B2 | 8/2010 | Palmer et al. |
| 7,780,700 B2 | 8/2010 | Frazier et al. |
| 7,811,305 B2 | 10/2010 | Balgobin et al. |
| 7,815,659 B2 | 10/2010 | Conlon et al. |
| 7,819,893 B2 | 10/2010 | Brady et al. |
| 7,828,815 B2 | 11/2010 | Mazzocchi et al. |
| 7,828,816 B2 | 11/2010 | Mazzocchi et al. |
| 7,833,240 B2 | 11/2010 | Okushi et al. |
| 7,842,053 B2 | 11/2010 | Chanduszko et al. |
| 7,846,175 B2 | 12/2010 | Bonnette et al. |
| 7,846,176 B2 | 12/2010 | Gilson et al. |
| 7,850,708 B2 | 12/2010 | Pal |
| 7,883,516 B2 | 2/2011 | Huang et al. |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi et al. |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | OBrien et al. |
| 8,052,640 B2 | 11/2011 | Fiorella et al. |
| 8,057,497 B1 | 11/2011 | Raju et al. |
| 8,057,507 B2 | 11/2011 | Horan et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,118,856 B2 | 2/2012 | Schreck et al. |
| 8,123,769 B2 | 2/2012 | Osborne |
| 8,137,376 B2 | 3/2012 | Clubb et al. |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,262,689 B2 | 9/2012 | Schneiderman et al. |
| 8,282,668 B2 | 10/2012 | McGuckin, Jr. et al. |
| 8,287,538 B2 | 10/2012 | Brenzel et al. |
| 8,298,257 B2 | 10/2012 | Sepetka et al. |
| RE43,882 E | 12/2012 | Hopkins et al. |
| 8,357,178 B2 | 1/2013 | Grandfield et al. |
| 8,357,179 B2 | 1/2013 | Grandfield et al. |
| 8,357,180 B2 | 1/2013 | Feller, III et al. |
| 8,357,893 B2 | 1/2013 | Xu et al. |
| 8,361,095 B2 | 1/2013 | Osborne |
| 8,361,110 B2 | 1/2013 | Chanduszko |
| 8,366,663 B2 | 2/2013 | Fiorella et al. |
| 8,409,215 B2 | 4/2013 | Sepetka et al. |
| 8,414,482 B2 | 4/2013 | Belson |
| 8,414,543 B2 | 4/2013 | McGuckin, Jr. et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,512,352 B2 | 8/2013 | Martin |
| 8,529,596 B2 | 9/2013 | Grandfield et al. |
| 8,545,526 B2 | 10/2013 | Martin et al. |
| 8,574,262 B2 | 11/2013 | Ferrera et al. |
| 8,574,915 B2 | 11/2013 | Zhang et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,690,907 B1 | 4/2014 | Janardhan et al. |
| 8,696,622 B2 | 4/2014 | Fiorella et al. |
| 8,702,652 B2 | 4/2014 | Fiorella et al. |

(56) References Cited

U.S. PATENT DOCUMENTS

| | | |
|---|---|---|
| 8,702,704 B2 | 4/2014 | Shelton, IV et al. |
| 8,702,724 B2 | 4/2014 | Olsen et al. |
| 8,777,919 B2 | 7/2014 | Kimura et al. |
| 8,777,976 B2 | 7/2014 | Brady et al. |
| 8,777,979 B2 | 7/2014 | Shrivastava et al. |
| 8,784,434 B2 | 7/2014 | Rosenbluth et al. |
| 8,784,441 B2 | 7/2014 | Rosenbluth et al. |
| 8,795,305 B2 | 8/2014 | Martin et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,852,205 B2 | 10/2014 | Brady et al. |
| 8,870,941 B2 | 10/2014 | Evans et al. |
| 8,900,265 B1 | 12/2014 | Ulm, III |
| 8,920,358 B2 | 12/2014 | Levine et al. |
| 8,939,991 B2 | 1/2015 | Krolik et al. |
| 8,945,143 B2 | 2/2015 | Ferrera et al. |
| 8,945,160 B2 | 2/2015 | Krolik et al. |
| 8,945,169 B2 | 2/2015 | Pal |
| 8,945,172 B2 | 2/2015 | Ferrera et al. |
| 8,956,399 B2 | 2/2015 | Cam et al. |
| 8,968,330 B2 | 3/2015 | Rosenbluth et al. |
| 9,011,481 B2 | 4/2015 | Aggerholm et al. |
| 9,039,749 B2 | 5/2015 | Shrivastava et al. |
| 9,072,537 B2 | 7/2015 | Grandfield et al. |
| 9,095,342 B2 | 8/2015 | Becking et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,758 B2 | 10/2015 | Figulla et al. |
| 9,161,766 B2 | 10/2015 | Slee et al. |
| 9,173,668 B2 | 11/2015 | Ulm, III |
| 9,173,688 B2 | 11/2015 | Dosta |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,211,132 B2 | 12/2015 | Bowman |
| 9,232,992 B2 | 1/2016 | Heidner et al. |
| 9,254,371 B2 | 2/2016 | Martin et al. |
| 9,301,769 B2 | 4/2016 | Brady et al. |
| 9,332,999 B2 | 5/2016 | Ray et al. |
| 9,402,707 B2 | 8/2016 | Brady et al. |
| 9,445,829 B2 | 9/2016 | Brady et al. |
| 9,456,834 B2 | 10/2016 | Folk |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,639 B2 | 5/2017 | Brady et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,898 B2 | 5/2017 | Palepu et al. |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,758,606 B2 | 9/2017 | Lambert et al. |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,651 B2 | 10/2017 | Harrah et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,304 B2 | 12/2017 | Horan et al. |
| 9,833,604 B2 | 12/2017 | Lam et al. |
| 9,833,625 B2 | 12/2017 | Waldhauser et al. |
| 9,901,434 B2 | 2/2018 | Hoffman |
| 9,918,720 B2 | 3/2018 | Marchand et al. |
| 9,939,361 B2 | 4/2018 | Gajji et al. |
| 10,016,206 B1 | 7/2018 | Yang |
| 10,070,878 B2 | 9/2018 | Ma |
| 10,098,651 B2 | 10/2018 | Marchand et al. |
| 10,201,360 B2 | 2/2019 | Vale et al. |
| 10,231,751 B2 | 3/2019 | Sos |
| 10,292,723 B2 | 5/2019 | Brady et al. |
| 10,299,811 B2 | 5/2019 | Brady et al. |
| 10,363,054 B2 | 7/2019 | Vale et al. |
| 10,376,274 B2 | 8/2019 | Farin et al. |
| 10,390,850 B2 | 8/2019 | Vale et al. |
| 10,524,811 B2 | 1/2020 | Marchand et al. |
| 10,531,942 B2 | 1/2020 | Eggers |
| 10,617,435 B2 | 4/2020 | Vale et al. |
| 10,722,257 B2 | 7/2020 | Skillrud et al. |
| 11,517,340 B2 | 12/2022 | Casey |
| 2001/0001315 A1 | 5/2001 | Bates et al. |
| 2001/0016755 A1 | 8/2001 | Addis |
| 2001/0037141 A1 | 11/2001 | Yee et al. |
| 2001/0037171 A1 | 11/2001 | Sato |
| 2001/0041909 A1 | 11/2001 | Tsugita et al. |
| 2001/0044632 A1 | 11/2001 | Daniel et al. |
| 2001/0049554 A1 | 12/2001 | Ruiz et al. |
| 2001/0051810 A1 | 12/2001 | Dubrul et al. |
| 2002/0004667 A1 | 1/2002 | Adams et al. |
| 2002/0016609 A1 | 2/2002 | Wensel et al. |
| 2002/0022859 A1 | 2/2002 | Hogendijk |
| 2002/0026211 A1 | 2/2002 | Khosravi et al. |
| 2002/0042627 A1 | 4/2002 | Brady et al. |
| 2002/0049468 A1 | 4/2002 | Streeter et al. |
| 2002/0052620 A1 | 5/2002 | Barbut |
| 2002/0058911 A1 | 5/2002 | Gilson et al. |
| 2002/0068954 A1 | 6/2002 | Foster |
| 2002/0072764 A1 | 6/2002 | Sepetka et al. |
| 2002/0082558 A1 | 6/2002 | Samson et al. |
| 2002/0091407 A1 | 7/2002 | Zadno-Azizi et al. |
| 2002/0095171 A1 | 7/2002 | Belef |
| 2002/0123765 A1 | 9/2002 | Sepetka et al. |
| 2002/0128680 A1 | 9/2002 | Pavolvic |
| 2002/0138094 A1 | 9/2002 | Borillo et al. |
| 2002/0143349 A1 | 10/2002 | Gifford, III et al. |
| 2002/0143362 A1 | 10/2002 | Macoviak et al. |
| 2002/0156455 A1 | 10/2002 | Barbut |
| 2002/0161393 A1 | 10/2002 | Demond et al. |
| 2002/0165576 A1 | 11/2002 | Boyle et al. |
| 2002/0173819 A1 | 11/2002 | Leeflang et al. |
| 2002/0183787 A1 | 12/2002 | Wahr et al. |

(56) References Cited

U.S. PATENT DOCUMENTS

| | | |
|---|---|---|
| 2002/0188276 A1 | 12/2002 | Evans et al. |
| 2002/0188314 A1 | 12/2002 | Anderson et al. |
| 2002/0193824 A1 | 12/2002 | Boylan et al. |
| 2002/0198588 A1 | 12/2002 | Armstrong et al. |
| 2003/0004536 A1 | 1/2003 | Boylan et al. |
| 2003/0004538 A1 | 1/2003 | Secrest et al. |
| 2003/0004540 A1 | 1/2003 | Linder et al. |
| 2003/0004542 A1 | 1/2003 | Wensel et al. |
| 2003/0009146 A1 | 1/2003 | Muni et al. |
| 2003/0009191 A1 | 1/2003 | Wensel et al. |
| 2003/0038447 A1 | 2/2003 | Cantele |
| 2003/0040772 A1 | 2/2003 | Hyodoh et al. |
| 2003/0050663 A1 | 3/2003 | Khachin et al. |
| 2003/0064151 A1 | 4/2003 | Klinedinst |
| 2003/0108224 A1 | 6/2003 | Ike |
| 2003/0114879 A1 | 6/2003 | Euteneuer et al. |
| 2003/0125798 A1 | 7/2003 | Martin |
| 2003/0130682 A1 | 7/2003 | Broome et al. |
| 2003/0144687 A1 | 7/2003 | Brady et al. |
| 2003/0144688 A1 | 7/2003 | Brady et al. |
| 2003/0153158 A1 | 8/2003 | Ho et al. |
| 2003/0153943 A1 | 8/2003 | Michael et al. |
| 2003/0153944 A1 | 8/2003 | Phung et al. |
| 2003/0163064 A1 | 8/2003 | Vrba et al. |
| 2003/0163158 A1 | 8/2003 | White |
| 2003/0171769 A1 | 9/2003 | Barbut |
| 2003/0171771 A1 | 9/2003 | Anderson et al. |
| 2003/0176884 A1 | 9/2003 | Berrada et al. |
| 2003/0187495 A1 | 10/2003 | Cully et al. |
| 2003/0195537 A1 | 10/2003 | Dubrul et al. |
| 2003/0195554 A1 | 10/2003 | Shen et al. |
| 2003/0199917 A1 | 10/2003 | Knudson et al. |
| 2003/0204202 A1 | 10/2003 | Palmer et al. |
| 2003/0208224 A1 | 11/2003 | Broome |
| 2003/0212430 A1 | 11/2003 | Bose et al. |
| 2003/0236533 A1 | 12/2003 | Wilson et al. |
| 2004/0064179 A1 | 4/2004 | Linder et al. |
| 2004/0068288 A1 | 4/2004 | Palmer et al. |
| 2004/0073243 A1 | 4/2004 | Sepetka et al. |
| 2004/0079429 A1 | 4/2004 | Miller et al. |
| 2004/0082962 A1 | 4/2004 | Demarais et al. |
| 2004/0082967 A1 | 4/2004 | Broome et al. |
| 2004/0088001 A1 | 5/2004 | Bosma et al. |
| 2004/0093065 A1 | 5/2004 | Yachia et al. |
| 2004/0098050 A1 | 5/2004 | Foerster et al. |
| 2004/0133231 A1 | 7/2004 | Maitland et al. |
| 2004/0133232 A1 | 7/2004 | Rosenbluth et al. |
| 2004/0138692 A1 | 7/2004 | Phung et al. |
| 2004/0153117 A1 | 8/2004 | Clubb et al. |
| 2004/0153118 A1 | 8/2004 | Clubb et al. |
| 2004/0199201 A1 | 10/2004 | Kellett et al. |
| 2004/0215318 A1 | 10/2004 | Kwitkin |
| 2004/0220663 A1 | 11/2004 | Rivelli |
| 2005/0033248 A1 | 2/2005 | Machida et al. |
| 2005/0033348 A1 | 2/2005 | Sepetka et al. |
| 2005/0038447 A1 | 2/2005 | Huffmaster |
| 2005/0038468 A1 | 2/2005 | Panetta et al. |
| 2005/0043759 A1 | 2/2005 | Chanduszko |
| 2005/0049619 A1 | 3/2005 | Sepetka et al. |
| 2005/0049669 A1 | 3/2005 | Jones et al. |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0058837 A1 | 3/2005 | Farnworth et al. |
| 2005/0059995 A1 | 3/2005 | Sepetka et al. |
| 2005/0085849 A1 | 4/2005 | Sepetka et al. |
| 2005/0090779 A1 | 4/2005 | Osypka |
| 2005/0090857 A1 | 4/2005 | Kusleika et al. |
| 2005/0125024 A1 | 6/2005 | Sepetka et al. |
| 2005/0149997 A1 | 7/2005 | Wolozin et al. |
| 2005/0171566 A1 | 8/2005 | Kanamaru |
| 2005/0173135 A1 | 8/2005 | Almen |
| 2005/0192627 A1 | 9/2005 | Whisenant et al. |
| 2005/0215942 A1 | 9/2005 | Abrahamson et al. |
| 2005/0216030 A1 | 9/2005 | Sepetka et al. |
| 2005/0216050 A1 | 9/2005 | Sepetka et al. |
| 2005/0228417 A1 | 10/2005 | Teitelbaum et al. |
| 2005/0251206 A1 | 11/2005 | Maahs et al. |
| 2005/0251209 A1 | 11/2005 | Saadat et al. |
| 2005/0267491 A1 | 12/2005 | Kellett et al. |
| 2005/0273135 A1 | 12/2005 | Chanduszko et al. |
| 2005/0283186 A1 | 12/2005 | Berrada et al. |
| 2005/0288686 A1 | 12/2005 | Sepetka et al. |
| 2006/0008332 A1 | 1/2006 | Greenberg et al. |
| 2006/0009798 A1 | 1/2006 | Callister et al. |
| 2006/0009799 A1 | 1/2006 | Kleshinski et al. |
| 2006/0020285 A1 | 1/2006 | Niermann |
| 2006/0020286 A1 | 1/2006 | Niermann |
| 2006/0030877 A1 | 2/2006 | Martinez et al. |
| 2006/0041228 A1 | 2/2006 | Vo et al. |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0064151 A1 | 3/2006 | Guterman et al. |
| 2006/0069424 A1 | 3/2006 | Acosta et al. |
| 2006/0074477 A1 | 4/2006 | Berthiaume et al. |
| 2006/0149313 A1 | 7/2006 | Arguello et al. |
| 2006/0155305 A1 | 7/2006 | Freudenthal et al. |
| 2006/0161187 A1 | 7/2006 | Levine et al. |
| 2006/0195137 A1 | 8/2006 | Sepetka et al. |
| 2006/0224177 A1 | 10/2006 | Finitsis |
| 2006/0224179 A1 | 10/2006 | Kucharczyk et al. |
| 2006/0229638 A1 | 10/2006 | Abrams et al. |
| 2006/0235501 A1 | 10/2006 | Igaki |
| 2006/0241677 A1 | 10/2006 | Johnson et al. |
| 2006/0282111 A1 | 12/2006 | Morsi |
| 2006/0287668 A1 | 12/2006 | Fawzi et al. |
| 2006/0287701 A1 | 12/2006 | Pal |
| 2006/0293706 A1 | 12/2006 | Shimon |
| 2007/0010857 A1 | 1/2007 | Sugimoto et al. |
| 2007/0032879 A1 | 2/2007 | Levine et al. |
| 2007/0088382 A1 | 4/2007 | Bei et al. |
| 2007/0088383 A1 | 4/2007 | Pal et al. |
| 2007/0100348 A1 | 5/2007 | Cauthen, III et al. |
| 2007/0118173 A1 | 5/2007 | Magnuson et al. |
| 2007/0149997 A1 | 6/2007 | Muller |
| 2007/0156170 A1 | 7/2007 | Hancock et al. |
| 2007/0165170 A1 | 7/2007 | Fukuda |
| 2007/0179527 A1 | 8/2007 | Skuri et al. |
| 2007/0191866 A1 | 8/2007 | Palmer et al. |
| 2007/0198028 A1 | 8/2007 | Miloslavski et al. |
| 2007/0198051 A1 | 8/2007 | Clubb et al. |
| 2007/0198075 A1 | 8/2007 | Levy |
| 2007/0208367 A1 | 9/2007 | Fiorella et al. |
| 2007/0208371 A1 | 9/2007 | French et al. |
| 2007/0225749 A1 | 9/2007 | Martin et al. |
| 2007/0233175 A1 | 10/2007 | Zaver et al. |
| 2007/0244505 A1 | 10/2007 | Gilson et al. |
| 2007/0270902 A1 | 11/2007 | Slazas et al. |
| 2007/0288054 A1 | 12/2007 | Tanaka et al. |
| 2008/0045881 A1 | 2/2008 | Teitelbaum et al. |
| 2008/0077227 A1 | 3/2008 | Ouellette et al. |
| 2008/0082107 A1 | 4/2008 | Miller et al. |
| 2008/0086190 A1 | 4/2008 | Ta |
| 2008/0091223 A1 | 4/2008 | Pokorney et al. |
| 2008/0097386 A1 | 4/2008 | Osypka |
| 2008/0109031 A1 | 5/2008 | Sepetka et al. |
| 2008/0109032 A1 | 5/2008 | Sepetka et al. |
| 2008/0119886 A1 | 5/2008 | Greenhalgh et al. |
| 2008/0125798 A1 | 5/2008 | Osborne et al. |
| 2008/0177296 A1 | 7/2008 | Sepetka et al. |
| 2008/0178890 A1 | 7/2008 | Townsend et al. |
| 2008/0183197 A1 | 7/2008 | Sepetka et al. |
| 2008/0183198 A1 | 7/2008 | Sepetka et al. |
| 2008/0183205 A1 | 7/2008 | Sepetka et al. |
| 2008/0188876 A1 | 8/2008 | Sepetka et al. |
| 2008/0188885 A1 | 8/2008 | Sepetka et al. |
| 2008/0188887 A1 | 8/2008 | Batiste |
| 2008/0200946 A1 | 8/2008 | Braun et al. |
| 2008/0200947 A1 | 8/2008 | Kusleika et al. |
| 2008/0215077 A1 | 9/2008 | Sepetka et al. |
| 2008/0221600 A1 | 9/2008 | Dieck et al. |
| 2008/0228209 A1 | 9/2008 | DeMello et al. |
| 2008/0234706 A1 | 9/2008 | Sepetka et al. |

(56) References Cited

U.S. PATENT DOCUMENTS

| | | |
|---|---|---|
| 2008/0243170 A1 | 10/2008 | Jenson et al. |
| 2008/0255596 A1 | 10/2008 | Jenson et al. |
| 2008/0262410 A1 | 10/2008 | Jenson et al. |
| 2008/0262528 A1 | 10/2008 | Martin |
| 2008/0262532 A1 | 10/2008 | Martin |
| 2008/0269871 A1 | 10/2008 | Eli |
| 2008/0275488 A1 | 11/2008 | Fleming |
| 2008/0275493 A1 | 11/2008 | Farmiga |
| 2008/0281350 A1 | 11/2008 | Sepetka et al. |
| 2008/0312681 A1 | 12/2008 | Ansel et al. |
| 2009/0005858 A1 | 1/2009 | Young et al. |
| 2009/0024157 A1 | 1/2009 | Anukhin |
| 2009/0030443 A1 | 1/2009 | Buser et al. |
| 2009/0062841 A1 | 3/2009 | Amplatz et al. |
| 2009/0069828 A1 | 3/2009 | Martin et al. |
| 2009/0076539 A1 | 3/2009 | Valaie |
| 2009/0088793 A1 | 4/2009 | Bagaoisan et al. |
| 2009/0088795 A1 | 4/2009 | Cahill |
| 2009/0105722 A1 | 4/2009 | Fulkerson et al. |
| 2009/0105737 A1 | 4/2009 | Fulkerson et al. |
| 2009/0105747 A1 | 4/2009 | Chanduszko et al. |
| 2009/0149881 A1 | 6/2009 | Vale et al. |
| 2009/0163851 A1 | 6/2009 | Holloway et al. |
| 2009/0177206 A1 | 7/2009 | Lozier et al. |
| 2009/0182336 A1 | 7/2009 | Brenzel et al. |
| 2009/0281610 A1 | 11/2009 | Parker |
| 2009/0281619 A1 | 11/2009 | Le et al. |
| 2009/0287229 A1 | 11/2009 | Ogdahl |
| 2009/0292297 A1 | 11/2009 | Ferrere |
| 2009/0292307 A1 | 11/2009 | Razack |
| 2009/0299393 A1 | 12/2009 | Martin et al. |
| 2009/0299403 A1 | 12/2009 | Chanduszko et al. |
| 2009/0306702 A1 | 12/2009 | Miloslavski et al. |
| 2009/0326636 A1 | 12/2009 | Hashimoto et al. |
| 2010/0004607 A1 | 1/2010 | Wilson et al. |
| 2010/0076482 A1 | 3/2010 | Shu et al. |
| 2010/0087850 A1 | 4/2010 | Razack |
| 2010/0087908 A1 | 4/2010 | Hilaire et al. |
| 2010/0114017 A1 | 5/2010 | Enker et al. |
| 2010/0125326 A1 | 5/2010 | Kalstad et al. |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnette et al. |
| 2010/0268265 A1 | 10/2010 | Krolik et al. |
| 2010/0274277 A1 | 10/2010 | Eaton |
| 2010/0318178 A1 | 12/2010 | Rapaport et al. |
| 2010/0324649 A1 | 12/2010 | Mattsson et al. |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009950 A1 | 1/2011 | Grandfield et al. |
| 2011/0015718 A1 | 1/2011 | Schreck |
| 2011/0022149 A1 | 1/2011 | Cox et al. |
| 2011/0040319 A1 | 2/2011 | Fulton, III |
| 2011/0054287 A1 | 3/2011 | Schultz |
| 2011/0054504 A1 | 3/2011 | Porter |
| 2011/0054514 A1 | 3/2011 | Arcand et al. |
| 2011/0054516 A1 | 3/2011 | Keegan et al. |
| 2011/0060212 A1 | 3/2011 | Slee et al. |
| 2011/0060359 A1 | 3/2011 | Hannes et al. |
| 2011/0106137 A1 | 5/2011 | Shimon |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0184456 A1 | 7/2011 | Grandfield et al. |
| 2011/0196414 A1 | 8/2011 | Porter et al. |
| 2011/0202088 A1 | 8/2011 | Eckhouse et al. |
| 2011/0208233 A1 | 8/2011 | McGuckin, Jr. et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0224707 A1 | 9/2011 | Miloslavski et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | di Palma et al. |
| 2012/0065660 A1 | 3/2012 | Ferrera et al. |
| 2012/0083823 A1 | 4/2012 | Shrivastava et al. |
| 2012/0083868 A1 | 4/2012 | Shrivastava et al. |
| 2012/0089216 A1 | 4/2012 | Rapaport et al. |
| 2012/0101510 A1 | 4/2012 | Lenker et al. |
| 2012/0116440 A1 | 5/2012 | Leynov et al. |
| 2012/0123466 A1 | 5/2012 | Porter et al. |
| 2012/0022572 A1 | 6/2012 | Braun et al. |
| 2012/0143230 A1 | 6/2012 | Sepetka et al. |
| 2012/0143237 A1 | 6/2012 | Cam et al. |
| 2012/0143317 A1 | 6/2012 | Cam et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0209312 A1 | 8/2012 | Aggerholm et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2012/0330350 A1 | 12/2012 | Jones et al. |
| 2013/0030460 A1 | 1/2013 | Marks et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144311 A1 | 6/2013 | Fung et al. |
| 2013/0144326 A1 | 6/2013 | Brady et al. |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0271788 A1 | 10/2013 | Utsunomiya |
| 2013/0277079 A1 | 10/2013 | Tsuzuki et al. |
| 2013/0281788 A1 | 10/2013 | Garrison |
| 2013/0325051 A1 | 12/2013 | Martin et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0046359 A1 | 2/2014 | Bowman et al. |
| 2014/0088678 A1 | 3/2014 | Wainwright et al. |
| 2014/0121672 A1 | 5/2014 | Folk |
| 2014/0128905 A1 | 5/2014 | Molaei |
| 2014/0134654 A1 | 5/2014 | Rudel et al. |
| 2014/0135812 A1 | 5/2014 | Divino et al. |
| 2014/0142598 A1 | 5/2014 | Fulton, III |
| 2014/0163367 A1 | 6/2014 | Eskuri |
| 2014/0180122 A1 | 6/2014 | Stigall et al. |
| 2014/0180377 A1 | 6/2014 | Bose et al. |
| 2014/0180397 A1 | 6/2014 | Gerberding et al. |
| 2014/0183077 A1 | 7/2014 | Rosendall et al. |
| 2014/0194911 A1 | 7/2014 | Johnson et al. |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0243881 A1 | 8/2014 | Lees et al. |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0303667 A1 | 10/2014 | Cox et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0372779 A1 | 12/2014 | Wong et al. |
| 2014/0379023 A1 | 12/2014 | Brady et al. |

(56) References Cited

U.S. PATENT DOCUMENTS

| | | |
|---|---|---|
| 2015/0018859 A1 | 1/2015 | Quick et al. |
| 2015/0018860 A1 | 1/2015 | Quick et al. |
| 2015/0032144 A1 | 1/2015 | Holloway |
| 2015/0080937 A1 | 3/2015 | Davidson |
| 2015/0112376 A1 | 4/2015 | Molaei et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0224133 A1 | 8/2015 | Ohri et al. |
| 2015/0250497 A1 | 9/2015 | Marks et al. |
| 2015/0257775 A1 | 9/2015 | Gilvarry et al. |
| 2015/0272716 A1 | 10/2015 | Pinchuk et al. |
| 2015/0297252 A1 | 10/2015 | Miloslavski et al. |
| 2015/0313617 A1 | 11/2015 | Grandfield et al. |
| 2015/0320431 A1 | 11/2015 | Ulm |
| 2015/0352325 A1 | 12/2015 | Quick |
| 2015/0359547 A1 | 12/2015 | Vale et al. |
| 2015/0366650 A1 | 12/2015 | Zi et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022269 A1 | 1/2016 | Ganske et al. |
| 2016/0022296 A1 | 1/2016 | Brady et al. |
| 2016/0045298 A1 | 2/2016 | Thinnes, Jr. et al. |
| 2016/0066921 A1 | 3/2016 | Seifert et al. |
| 2016/0100928 A1 | 4/2016 | Lees et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0303381 A1 | 10/2016 | Pierce et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020542 A1 | 1/2017 | Martin et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0056061 A1 | 3/2017 | Ogle et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0112647 A1 | 4/2017 | Sachar et al. |
| 2017/0113023 A1 | 4/2017 | Steingisser et al. |
| 2017/0119409 A1 | 5/2017 | Ma |
| 2017/0143465 A1 | 5/2017 | Ulm, III |
| 2017/0147765 A1 | 5/2017 | Mehta |
| 2017/0150979 A1 | 6/2017 | Ulm |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0189041 A1 | 7/2017 | Cox et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0055884 A1 | 3/2018 | Barclay Dupere et al. |
| 2018/0140315 A1 | 5/2018 | Bowman et al. |
| 2018/0206865 A1 | 7/2018 | Martin et al. |
| 2018/0207399 A1 | 7/2018 | Chou et al. |
| 2018/0263650 A1 | 9/2018 | Iwanami et al. |
| 2018/0325537 A1 | 11/2018 | Shamay et al. |
| 2018/0326024 A1 | 11/2018 | Prochazka et al. |
| 2018/0344338 A1 | 12/2018 | Brady et al. |
| 2019/0000492 A1 | 1/2019 | Casey et al. |
| 2019/0015061 A1 | 1/2019 | Liebskind et al. |
| 2019/0167284 A1 | 6/2019 | Friedman et al. |
| 2019/0239907 A1 | 8/2019 | Brady et al. |
| 2019/0292273 A1 | 9/2019 | Hanotin et al. |
| 2019/0374239 A1 | 12/2019 | Martin et al. |
| 2019/0380723 A1 | 12/2019 | Grandfield et al. |
| 2019/0388097 A1 | 12/2019 | Girdhar et al. |
| 2020/0000483 A1 | 1/2020 | Brady et al. |
| 2020/0009150 A1 | 1/2020 | Chamorro Sanchez |
| 2020/0085444 A1 | 3/2020 | Vale et al. |
| 2020/0100804 A1 | 4/2020 | Casey et al. |
| 2020/0297364 A1 | 9/2020 | Choe et al. |
| 2020/0305900 A1* | 10/2020 | Vale ............... A61B 17/320725 |
| 2020/0390459 A1 | 12/2020 | Casey et al. |

(56) References Cited

U.S. PATENT DOCUMENTS

| | | | |
|---|---|---|---|
| 2021/0007757 | A1 | 1/2021 | Casey et al. |
| 2021/0228223 | A1 | 7/2021 | Casey et al. |

FOREIGN PATENT DOCUMENTS

| | | | |
|---|---|---|---|
| CN | 102316809 A | 1/2012 | |
| CN | 2557083 Y | 7/2012 | |
| CN | 102596098 A | 7/2012 | |
| CN | 104042304 A | 9/2014 | |
| CN | 105208950 A | 12/2015 | |
| CN | 105662532 A | 6/2016 | |
| CN | 205359559 U | 7/2016 | |
| CN | 107530090 A | 1/2018 | |
| CN | 208582467 U | 3/2019 | |
| DE | 202009001951 U1 | 4/2010 | |
| DE | 102009056450 A1 | 6/2011 | |
| DE | 102010010849 A1 | 9/2011 | |
| DE | 102010014778 A1 | 10/2011 | |
| DE | 102010024085 A1 | 12/2011 | |
| DE | 102011014586 B3 | 9/2012 | |
| EP | 1153581 A1 | 11/2001 | |
| EP | 2301450 A1 | 3/2011 | |
| EP | 2438891 A1 | 4/2012 | |
| EP | 2628455 A1 | 8/2013 | |
| EP | 3156004 A1 | 4/2017 | |
| EP | 3593742 A1 | 1/2020 | |
| EP | 3669802 A1 | 6/2020 | |
| EP | 3858291 A1 | 8/2021 | |
| GB | 2427554 A | 1/2007 | |
| GB | 2494820 A | 3/2013 | |
| JP | H0919438 A | 1/1997 | |
| JP | 2014511223 A | 5/2014 | |
| JP | 2014525796 A | 10/2014 | |
| JP | 2015-505250 A | 2/2015 | |
| JP | 2019-526365 A | 5/2016 | |
| JP | 2016-513505 A | 9/2019 | |
| VN | 103764049 A | 4/2014 | |
| WO | 9424926 A1 | 11/1994 | |
| WO | 9727808 A1 | 8/1997 | |
| WO | 9738631 A1 | 10/1997 | |
| WO | 9920335 A1 | 4/1999 | |
| WO | 9956801 A2 | 11/1999 | |
| WO | 9960933 A1 | 12/1999 | |
| WO | 0121077 A1 | 3/2001 | |
| WO | 0202162 A2 | 1/2002 | |
| WO | 0211627 A2 | 2/2002 | |
| WO | 0243616 A2 | 6/2002 | |
| WO | 02070061 A1 | 9/2002 | |
| WO | 02094111 A2 | 11/2002 | |
| WO | 03002006 A1 | 1/2003 | |
| WO | 03030911 A1 | 4/2003 | |
| WO | 03051448 A2 | 6/2003 | |
| WO | 2004028571 A2 | 4/2004 | |
| WO | 2004056275 A1 | 7/2004 | |
| WO | 2005000130 A1 | 1/2005 | |
| WO | 2005027779 A2 | 3/2005 | |
| WO | 2006021407 A2 | 3/2006 | |
| WO | 2006031410 A2 | 3/2006 | |
| WO | 2006107641 A2 | 10/2006 | |
| WO | 2006135823 A2 | 12/2006 | |
| WO | 2007054307 A2 | 5/2007 | |
| WO | 2007068424 A2 | 6/2007 | |
| WO | 2008034615 A2 | 3/2008 | |
| WO | 2008051431 A1 | 5/2008 | |
| WO | 2008131116 A1 | 10/2008 | |
| WO | 2008135823 A1 | 11/2008 | |
| WO | 2009031338 A1 | 3/2009 | |
| WO | 2009076482 A1 | 6/2009 | |
| WO | 2009086482 A1 | 7/2009 | |
| WO | 2009105710 A1 | 8/2009 | |
| WO | 2010010545 A1 | 1/2010 | |
| WO | 2010046897 A1 | 4/2010 | |
| WO | 2010075565 A2 | 7/2010 | |
| WO | 2010102307 A1 | 9/2010 | |
| WO | 2010146581 A1 | 12/2010 | |
| WO | 2011013556 A1 | 2/2011 | |
| WO | 2011066961 A1 | 6/2011 | |
| WO | 2011082319 A1 | 7/2011 | |
| WO | 2011095352 A1 | 8/2011 | |
| WO | 2011106426 A1 | 9/2011 | |
| WO | 2011110316 A1 | 9/2011 | |
| WO | 2011135556 A1 | 11/2011 | |
| WO | 2012052982 A1 | 4/2012 | |
| WO | 2012064726 A1 | 5/2012 | |
| WO | 2012081020 A1 | 6/2012 | |
| WO | 2012110619 A1 | 8/2012 | |
| WO | 2012120490 A2 | 9/2012 | |
| WO | 2012156924 A1 | 11/2012 | |
| WO | 2013016435 A1 | 1/2013 | |
| WO | 2013072777 A2 | 5/2013 | |
| WO | 2013105099 A2 | 7/2013 | |
| WO | 2013109756 A2 | 7/2013 | |
| WO | 2013187927 A1 | 12/2013 | |
| WO | 2014047650 A1 | 3/2014 | |
| WO | 2014081892 A1 | 5/2014 | |
| WO | 2014139845 A1 | 9/2014 | |
| WO | 2014169266 A1 | 10/2014 | |
| WO | 2014178198 A1 | 11/2014 | |
| WO | 2015061365 A1 | 4/2015 | |
| WO | 2015103547 A1 | 7/2015 | |
| WO | 2015134625 A1 | 9/2015 | |
| WO | 2015179324 A2 | 11/2015 | |
| WO | 2015189354 A1 | 12/2015 | |
| WO | 2016010995 A1 | 1/2016 | |
| WO | 2016089451 A1 | 6/2016 | |
| WO | 2017089424 A1 | 6/2017 | |
| WO | WO 2017/090472 A1 | 6/2017 | |
| WO | WO 2017/090473 A1 | 6/2017 | |
| WO | WO 2017/103686 A2 | 6/2017 | |
| WO | WO 2017/161204 A1 | 9/2017 | |
| WO | WO 2020/039082 A1 | 2/2020 | |
| WO | WO 2021/113302 A1 | 6/2021 | |

OTHER PUBLICATIONS

Notch definition & Meaning, Dictionary.com, https://www.dictionary.com/browse/notch, accessed May 5, 2022, copyright 2022 Dictionary.com, LLC (Year: 2022).*

Sinusoidal-Definition, Meaning &Synonyms, Vocabulary.com, https://www.vocabulary.com/dictionary/sinusoidal, accessed May 5, 2022, copyright 2022 Vocabulary.com, Inc., a division of IXL Learning (Year: 2022).*

Comprise definition in the Cambridge English Dictionary, https://dictionary.cambridge/org/US/dictionary/english/comprise, accessed Apr. 21, 2023, copyright Cambridge University Press & Assessment 2023 (Year: 2023).*

Search Report issued in corresponding Chinese Patent Application No. 201680080064.4 dated Jun. 9, 2020 (English translation only).

* cited by examiner

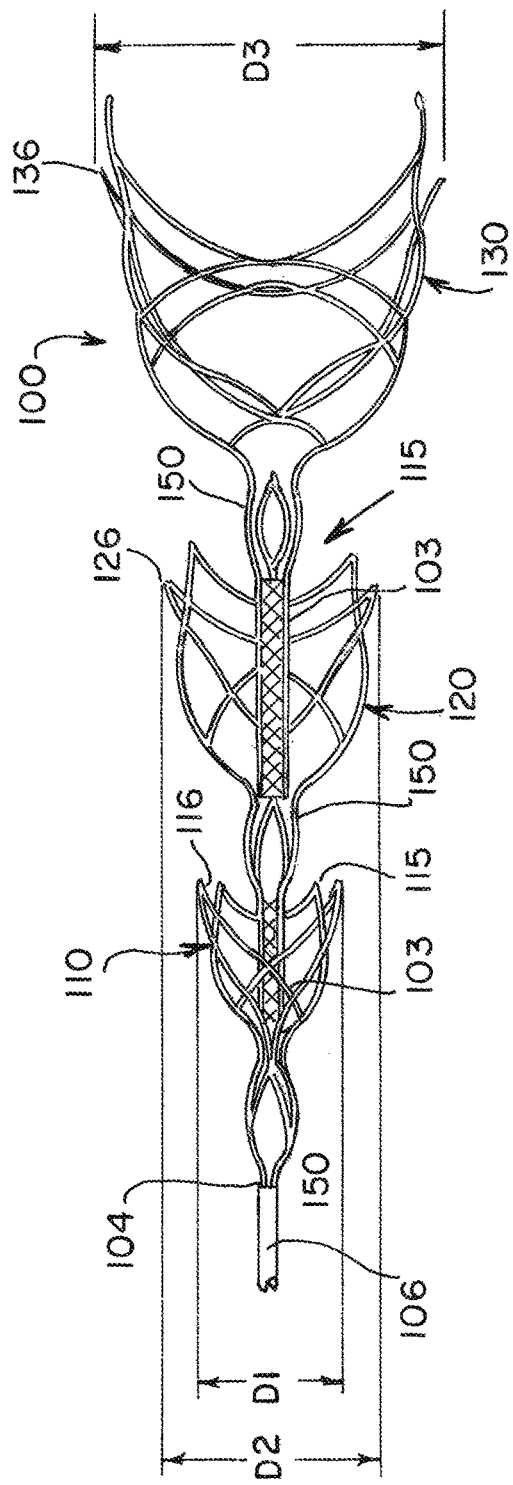
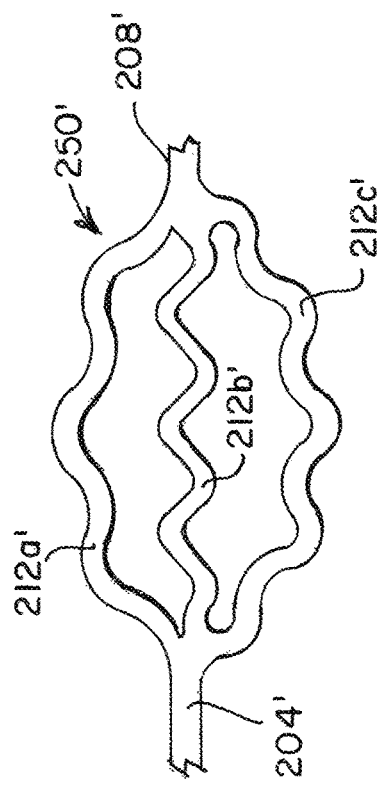
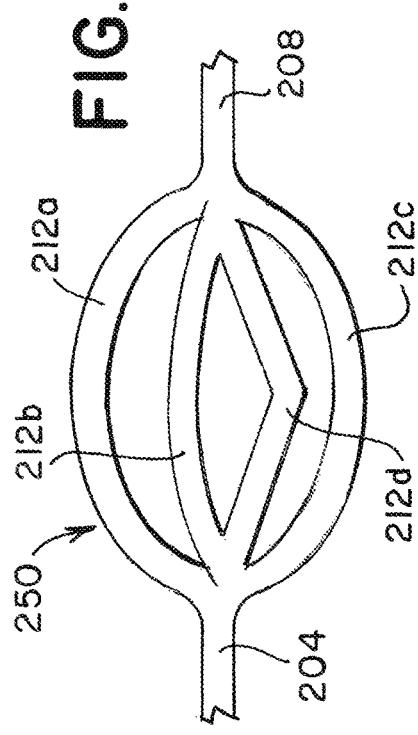

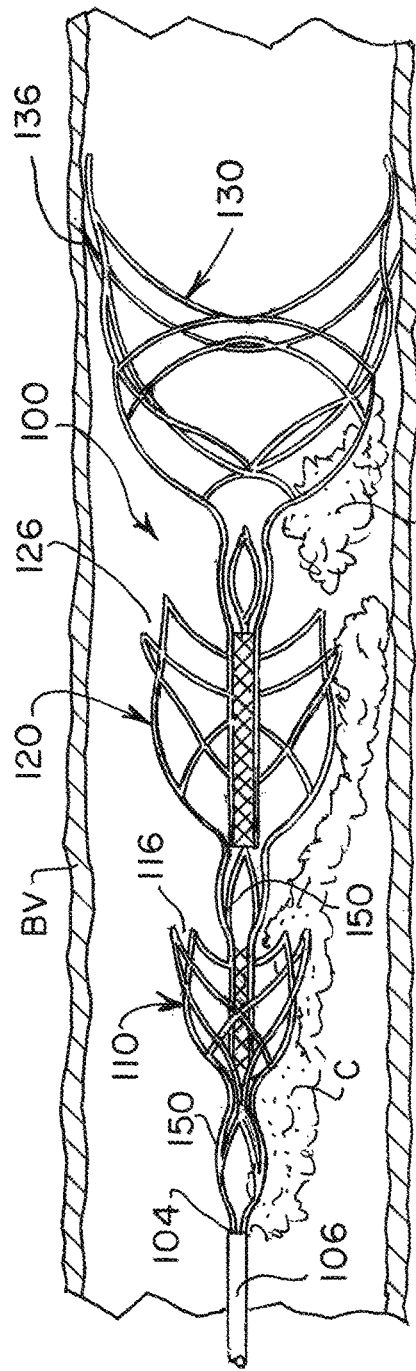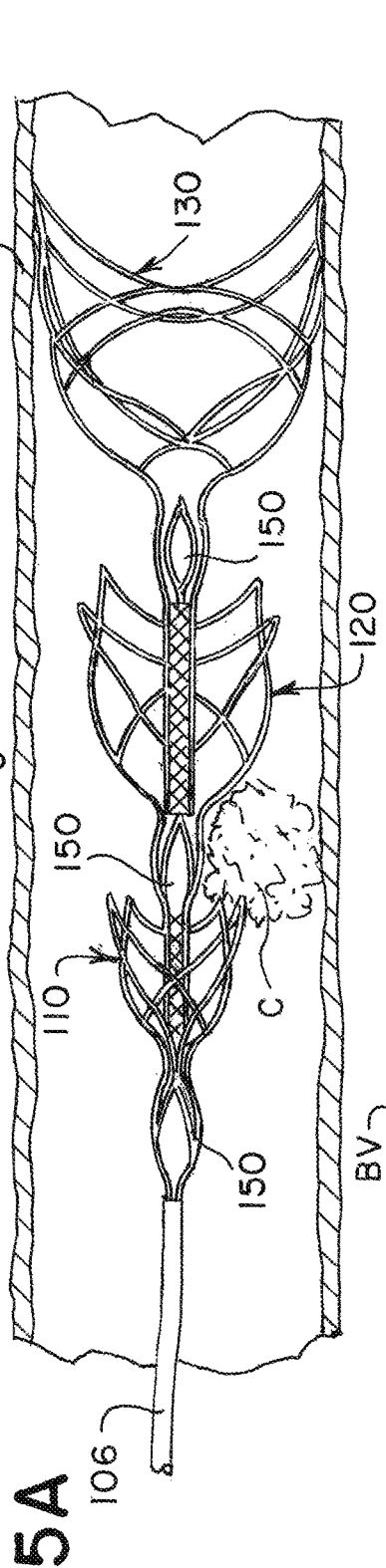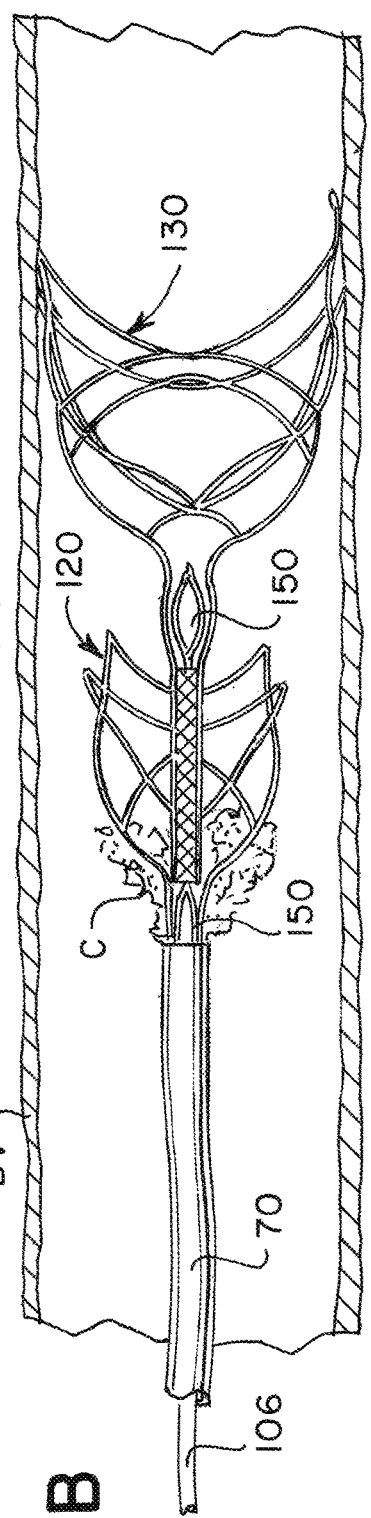

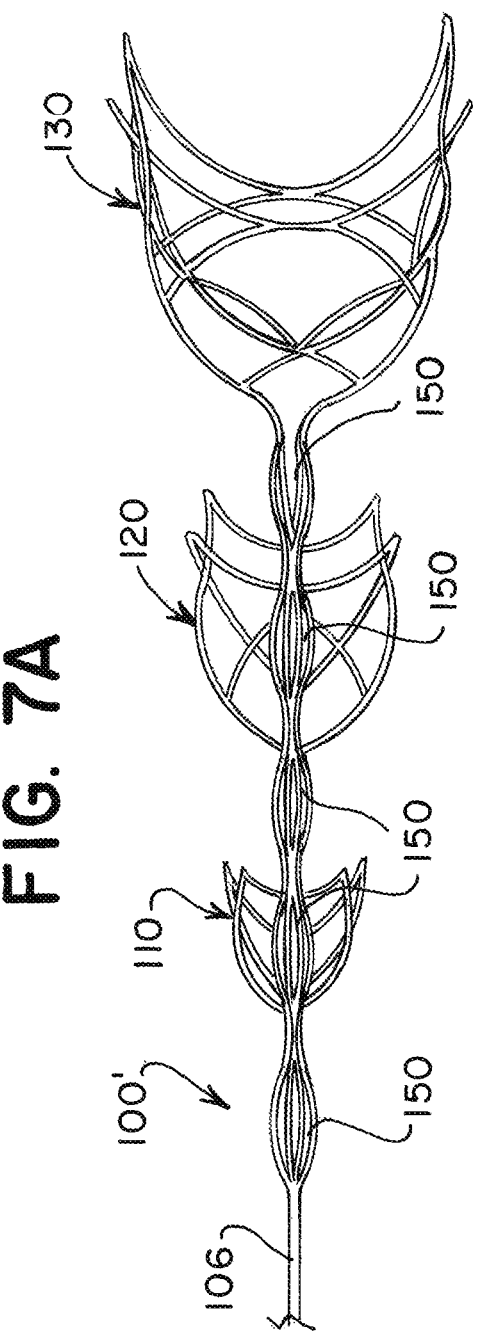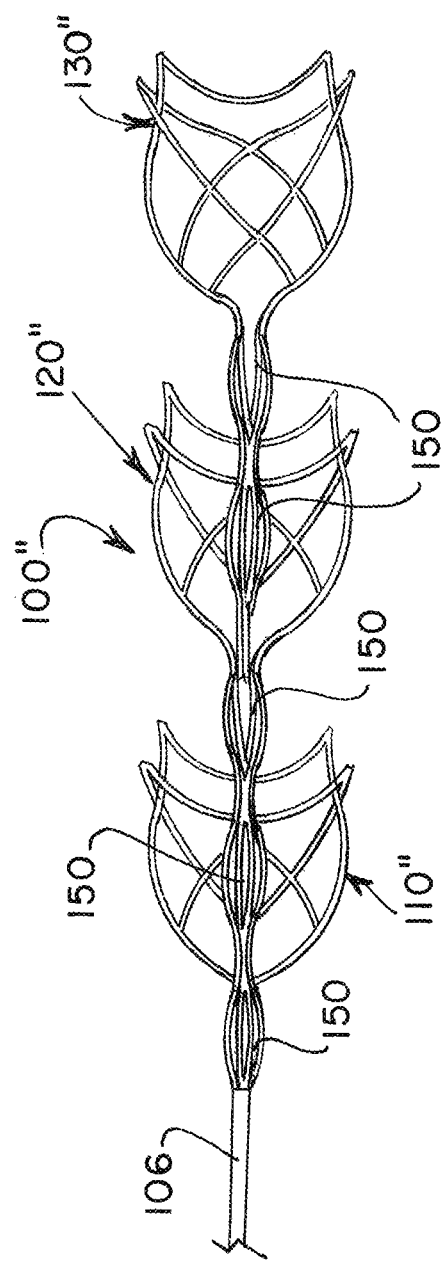

CLOT RETRIEVAL DEVICE FOR REMOVING CLOT FROM A BLOOD VESSEL

FIELD

The present disclosure generally relates to devices and methods for removing blockages from blood vessels during intravascular medical treatments.

BACKGROUND

Clot retrieval devices are used in mechanical thrombectomy for endovascular intervention, often in cases where patients are suffering from conditions such as acute ischemic stroke (AIS), myocardial infarction (MI), and pulmonary embolism (PE). Acute obstructions may include clot, misplaced devices, migrated devices, large emboli and the like. Thromboembolism occurs when part or all of a thrombus breaks away from the blood vessel wall. This clot (now called an embolus) is then carried in the direction of blood flow. An ischemic stroke may result if the clot lodges in the cerebral vasculature. A pulmonary embolism may result if the clot originates in the venous system or in the right side of the heart and lodges in a pulmonary artery or branch thereof. Clots may also develop and block vessels locally without being released in the form of an embolus—this mechanism is common in the formation of coronary blockages. There are significant challenges associated with designing clot removal devices that can deliver high levels of performance. First, there are a number of access challenges that make it difficult to deliver devices. In cases where access involves navigating the aortic arch (such as coronary or cerebral blockages) the configuration of the arch in some patients makes it difficult to position a guide catheter. These difficult arch configurations are classified as either type 2 or type 3 aortic arches with type 3 arches presenting the most difficulty.

The tortuosity challenge is even more severe in the arteries approaching the brain. For example it is not unusual at the distal end of the internal carotid artery that the device will have to navigate a vessel segment with a 180° bend, a 90° bend and a 360° bend in quick succession over a few centimetres of vessel. In the case of pulmonary embolisms, access is through the venous system and then through the right atrium and ventricle of the heart. The right ventricular outflow tract and pulmonary arteries are delicate vessels that can easily be damaged by inflexible or high profile devices. For these reasons it is desirable that the clot retrieval device be compatible with as low profile and flexible a guide catheter as possible.

Second, the vasculature in the area in which the clot may be lodged is often fragile and delicate. For example neurovascular vessels are more fragile than similarly sized vessels in other parts of the body and are in a soft tissue bed. Excessive tensile forces applied on these vessels could result in perforations and hemorrhage. Pulmonary vessels are larger than those of the cerebral vasculature, but are also delicate in nature, particularly those more distal vessels.

Third, the clot may comprise any of a range of morphologies and consistencies. For example, clot can be difficult to grip and improper grip can lead to fragmentation which may cause embolization. Long strands of softer clot material may also tend to lodge at bifurcations or trifurcations, resulting in multiple vessels being simultaneously occluded over significant lengths. More mature and organized clot material is likely to be less compressible than softer fresher clot, and under the action of blood pressure it may distend the compliant vessel in which it is lodged. Furthermore the inventors have discovered that the properties of the clot may be significantly changed by the action of the devices interacting with it. In particular, compression of a blood clot causes dehydration of the clot and results in a dramatic increase in both clot stiffness and coefficient of friction.

The challenges described above need to be overcome for any devices to provide a high level of success in removing clot and restoring flow. Existing devices do not adequately address these challenges, particularly those challenges associated with vessel trauma and clot properties.

SUMMARY

It is an object of the present design to provide devices and methods to meet the above-stated needs. It is therefore desirable for a clot retrieval device to remove clot from cerebral arteries in patients suffering AIS, from coronary native or graft vessels in patients suffering from MI, and from pulmonary arteries in patients suffering from PE and from other peripheral arterial and venous vessels in which clot is causing an occlusion.

In some examples, the device includes pinch features along at the site of an occlusion (e.g., in the mid internal carotid artery (ICA)). The device can be configured to reperfuse a vessel and/or remove a clot that has a fibrin core. In some examples, the fibrin core can be in a mid- or distal-position in the clot surrounded by relatively soft thrombus.

In some examples, the device is configured to remove a clot in the M1 bifurcation.

In some examples, the device is configured to remove a clot in the M2 bifurcation.

In some examples, the device includes a first scaffolding section; a second scaffolding section distal of the first scaffolding section by a first hinged element including a pinching cell including a collapsed state and an expanded state configured to pinch at least a portion of a clot; a third scaffolding section distal of the second scaffolding section by a second hinged strut element including a pinching cell including a collapsed state and an expanded state configured to pinch at least a portion of the clot; and an outer diameter of the third scaffolding section being greater than an outer diameter of the second scaffolding section which is greater than an outer diameter of the first scaffolding section.

In some examples, each scaffolding section includes a plurality of struts that form an array of closed cells.

In some examples, the device includes a hinged element with a pinching cell proximal of the first scaffolding section and connected to a distal end of a shaft.

In some examples, each pinching cell has at least one of an eyelet, a notched element to embed with clot, or a sinusoidal strut pattern.

In some examples, the first scaffolding section is extended at least partially over an inner body including a flow channel configured to engage the clot and restore blood flow through the clot, the inner body including a collapsed state and an expanded state. The outer diameters of the first scaffolding section and second scaffolding section is greater than an outer diameter of the inner body in the deployed configuration to define a clot reception space between the inner body and the separate first and second scaffolding sections. The device further includes a first clot inlet mouth between the first and second scaffolding section. In some examples, each hinged element is configured to self-align the corresponding scaffolding sections to articulate in bends of the vasculature.

In some examples, the first scaffolding section is eccentrically coupled over the inner body. In some examples, the second scaffolding section is extended at least partially over an inner body including a flow channel configured to engage the clot and restore blood flow through the clot, the inner body of the second scaffolding section includes a collapsed state and an expanded state. Each hinge can be being the only point of contact between respective clot scaffolding sections.

In some examples, a proximal end of each respective flow channel is joined at a respective proximal end of a respective scaffolding section and a distal end of each respective flow channel joined at a respective subsequent scaffolding section.

In some examples, a second clot inlet mouth is positioned between the second scaffolding section and the third scaffolding section.

In some examples, each of the first, second, and third scaffolding sections includes an open distal end.

In some examples, each of the first, second, and third scaffolding sections includes a closed proximal end.

In some examples, each of the first, second, and third scaffolding sections comprise a plurality struts formed of closed cells, the distal end of at least one of the first, second, and third scaffolding sections terminates in at least one distal apex free from connection to an adjacent closed cell of the respective scaffolding sections.

In some examples, the at least one distal apex is a petal or leaf member configured to open up in a flower-like manner and expand in one or more bifurcations of the vasculature to remove the clot.

In some examples, closed cells of the first scaffolding section are smaller than cells of the second scaffolding section.

In some examples, closed cells of the second scaffolding section are smaller than cells of the third scaffolding section.

In some examples, each of the first, second, and third scaffolding sections proximally taper from an open distal end to a closed proximal end.

In some examples, each of the first, second, and third scaffolding sections includes a plurality struts formed of closed cells, the distal end of at least one of the first, second, and third scaffolding sections terminates in crowns with no distal connecting elements. At least one of the crowns is configured to pivot open in a flower-like manner as clot engages therewith.

In some examples, expanding the clot removal device causes that at least one of pinching cells, the first scaffolding section, the second scaffolding section, and the third scaffolding section to deform at least a portion of the clot.

In some examples, each pinching cell includes a plurality of bowed strut members configured to actuate and pinch the clot from a blood vessel between the pair of bowed strut members. In some examples, the strut members form a network of struts operable to engage and then pinch at least a portion of a clot. In some examples, the bowed strut members being positioned about one or more central strut members, each strut member joined at common respective proximal and distal ends. In some examples, each of the pinching cells is configured to pinch the clot on movement from the collapsed state to a clot pinching state of the expanded state until a portion of the clot is compressed between a respective pinching cell. In some examples, a ratio of a diameter of each pinching cell between the collapsed state and expanded state is from approximately 1.5:1 to 4:1.

In some examples, the third scaffolding section includes a constrained delivery configuration and an at least partially constrained clot pinching configuration, at least a portion of the third scaffolding section being configured to engage clot in the expanded state and to pinch clot on movement from the expanded state to the clot pinching configuration.

In some examples, the third scaffolding section includes a clot pinching structure configured to pinch clot on movement from the expanded state to the clot pinching configuration.

In some examples, the clot pinching structure includes a spiral form.

In some examples, the clot pinching structure includes a non-tubular planar form.

In some examples, the third scaffolding section includes a longitudinal axis and the clot pinching structure extends around the longitudinal axis in a spiral.

In some examples, the third scaffolding section is configured to exert an outward radial force when deployed within a lumen whose inner diameter is lower than that of the expanded state. In some examples, the outward radial force can vary in a generally sinusoidal pattern along a length of the third scaffolding section, the generally sinusoidal pattern including a wave pattern and the amplitude generally consistent along the length. In some examples, the outward radial force can vary in a generally sinusoidal pattern along a length of the third scaffolding section, the generally sinusoidal pattern including a wave pattern and the amplitude generally decreasing along the length being higher at a proximal end of the third scaffolding section and lower at the distal end of the third scaffolding section.

In some examples, at least five (5) pinching cells are positioned end-to-end between proximal and distal ends of device.

In some examples, at least three (3) pinching cells are positioned end-to-end between proximal and distal ends of device.

In some examples, a clot removal device is disclosed including a first scaffolding section; a second scaffolding section distal of the first scaffolding section by a first hinged element including a pinching cell including a collapsed state and an expanded state configured to pinch at least a portion of a clot; and a third scaffolding section distal of the second scaffolding section by a second hinged strut element including a pinching cell including a collapsed state and an expanded state configured to pinch at least a portion of a clot.

In some examples, a method for removing a clot is disclosed. The method includes delivering a clot removal device in a blood vessel at or adjacent a site of a clot, the clot removal device including a collapsed state and an expanded state and including a first scaffolding section, a second scaffolding section distal of the first scaffolding section by a first hinged element including a pinching cell including a collapsed state and an expanded state configured to pinch at least a portion of a clot; a third scaffolding section distal of the second scaffolding section by a second hinged strut element including a pinching cell including a collapsed state and an expanded state configured to pinch at least a portion of a clot. The method includes embedding at least one of cells and scaffolding sections with at least a portion of the clot in a clot reception space by expanding the clot removal device from the collapsed state to the expanded state; and removing at least a portion of the clot by withdrawing the clot removal device.

In some examples, an outer diameter of the third scaffolding section is greater than an outer diameter of the second scaffolding section which is greater than an outer diameter of the first scaffolding section.

In some examples, an outer diameter of the third scaffolding section being approximately equal to an outer diameter of the second scaffolding section which is approximately equal to an outer diameter of the first scaffolding section.

In some examples, the method includes sequentially positioning at least five (5) pinching cells end-to-end.

In some examples, the method includes sequentially positioning at least three (3) pinching cells end-to-end.

In some examples, the step of embedding further includes expanding at least one of the first, second, and third scaffolding sections and urging at least the portion of the clot in the clot reception space.

In some examples, the method includes resheathing a microcatheter at least partially over the device to grip, pinch, and/or tweeze, by at least one of the cells or section, the clot.

In some examples, the method includes capturing at least some of the clot using the first scaffolding section.

In some examples, the method includes capturing at least some of the clot using the second scaffolding section.

In some examples, the method includes capturing at least some of the clot using the third scaffolding section.

In some examples, the method includes pinching, gripping, and/or tweezing at least some of the clot using at least one of the one or more pinching cells.

In some examples, the method includes expanding the clot removal device so that the scaffolding sections deform at least a portion of the clot between an inlet between the first and second scaffolding sections and/or between the second and third scaffolding sections.

In some examples, the third scaffolding section includes a constrained delivery configuration and an at least partially constrained clot pinching configuration, the method including engaging and pinching clot, by at least a portion of the third scaffolding section, on movement from the expanded state to the clot pinching configuration.

In some examples, the method includes exerting an outward radial force, by the third scaffolding section, when deployed within a lumen whose inner diameter is lower than that of the expanded state.

In some examples, the method includes varying the outward radial force in a generally sinusoidal pattern along a length of the third scaffolding section, the generally sinusoidal pattern including a wave pattern and the amplitude generally consistent along the length.

In some examples, the method includes varying the outward radial force in a generally sinusoidal pattern along a length of the third scaffolding section, the generally sinusoidal pattern including a wave pattern and the amplitude generally decreasing along the length being higher at a proximal end of the third scaffolding section and lower at a distal end of the third scaffolding section.

In some examples, the method includes terminating a distal end of at least one of the first, second, and third scaffolding sections in at least one distal apex free from connection to an adjacent closed cell of the respective scaffolding sections.

In some examples, the method includes opening up the at least one distal apex in a flower-like manner in the expanded state; and expand the at least one distal apex in one or more bifurcations of the vasculature to remove the clot, the at least one distal apex being a petal or leaf member hingedly connected to at least one strut of the respective scaffolding sections.

In some examples, the method includes extending the first scaffolding section at least partially over an inner body including a flow channel configured to engage the clot and restore blood flow through the clot, the inner body including a collapsed state and an expanded state; the outer diameters of the first scaffolding section and second scaffolding section being greater than an outer diameter of the inner body in the deployed configuration to define a clot reception space between the inner body and the separate first and second scaffolding sections, the device further including a first clot inlet mouth between the first and second scaffolding section.

In some examples, the method includes each hinged element self-aligning the corresponding scaffolding sections to articulate in bends of the vasculature.

In some examples, the method includes eccentrically coupling the first scaffolding section over the inner body.

Other aspects and features of the present disclosure will become apparent to those of ordinary skill in the art, upon reviewing the following detailed description in conjunction with the accompanying figures.

BRIEF DESCRIPTION OF THE DRAWINGS

The above and further aspects of this disclosure are further discussed with the following description of the accompanying drawings, in which like numerals indicate like structural elements and features in various figures. The drawings are not necessarily to scale, emphasis instead being placed upon illustrating principles of the disclosure. The figures depict one or more implementations of the inventive devices, by way of example only, not by way of limitation. It is expected that those of skill in the art can conceive of and combining elements from multiple figures to better suit the needs of the user.

FIG. 1 illustrates a side view of a clot retrieval device of this disclosure.

FIG. 2A depicts a close-up view of an example pinching cell.

FIG. 2B depicts a close-up view of an example pinching cell.

FIG. 4 depicts a side view of an example clot retrieval device of this disclosure in an example blood vessel in use with an example clot.

FIG. 5A depicts a side view of the example clot retrieval device of FIG. 4 in an example blood vessel in use with an example clot.

FIG. 5B depicts a side view of the example clot retrieval device of FIG. 4 in an example blood vessel in use with an example clot.

FIG. 7A depicts a side view of another example clot retrieval device.

FIG. 7B depicts a side view of another example clot retrieval device.

DETAILED DESCRIPTION

Figure 2C:
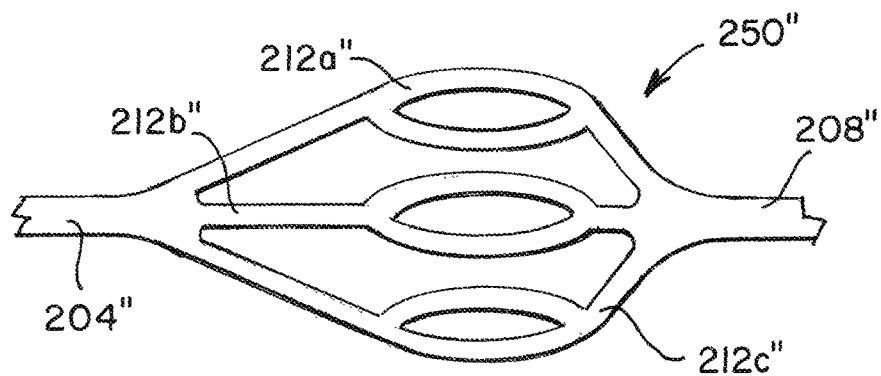
FIG. 2C depicts a close-up view of an example pinching cell.

Specific examples of the present disclosure are now described in detail with reference to the Figures, where identical reference numbers indicate elements which are functionally similar or identical. The examples address many of the deficiencies associated with traditional catheters, such as inefficient clot removal and inaccurate deployment of catheters to a target site.

Accessing the various vessels within the vascular, whether they are coronary, pulmonary, or cerebral, involves well-known procedural steps and the use of a number of conventional, commercially-available accessory products. These products, such as angiographic materials and guidewires are widely used in laboratory and medical procedures. When these products are employed in conjunction with the system and methods of this disclosure in the description below, their function and exact constitution are not described in detail.

The following detailed description is merely exemplary in nature and is not intended to limit the disclosure or the application and uses of the disclosure. Although the description of the disclosure is in many cases in the context of treatment of intracranial arteries, the disclosure may also be used in other body passageways as previously described.

It will be apparent from the foregoing description that, while particular embodiments of the present disclosure have been illustrated and described, various modifications can be made without departing from the spirit and scope of the disclosure. For example, while the embodiments described herein refer to particular features, the disclosure includes embodiments having different combinations of features. The disclosure also includes embodiments that do not include all of the specific features described. Specific embodiments of the present disclosure are now described in detail with reference to the figures, wherein identical reference numbers indicate identical or functionality similar elements. The terms "distal" or "proximal" are used in the following description with respect to a position or direction relative to the treating physician. "Distal" or "distally" are a position distant from or in a direction away from the physician. "Proximal" or "proximally" or "proximate" are a position near or in a direction toward the physician.

Accessing cerebral, coronary and pulmonary vessels involves the use of a number of commercially available products and conventional procedural steps. Access products such as guidewires, guide catheters, angiographic catheters and microcatheters are described elsewhere and are regularly used in catheter lab procedures. It is assumed in the descriptions below that these products and methods are employed in conjunction with the device and methods of this disclosure and do not need to be described in detail.

The following detailed description is merely exemplary in nature and is not intended to limit the disclosure or the application and uses of the disclosure. Although the description of the disclosure is in many cases in the context of treatment of intracranial arteries, the disclosure may also be used in other body passageways as previously described.

A common theme across many of the disclosed designs is a multi-layer construction in which the device in certain instances can include an outer expandable member within which, at times, can include an inner expandable member, both members being directly or indirectly connected to an elongate shaft. Turning to FIG. 1, one example device 100 according to this disclosure is illustrated. In particular, device 100 is shown in a side view whereby a proximal end 104 of device 100 is connected to distal end of an elongate shaft 106. As shown, the distal end of shaft 106 extends interior of the artery and a proximal end that extends exterior of the artery. Device 100 can include a plurality of pinching cells 150, including a first cell 150 at or adjacent proximal end 104 and connected to shaft 106. The first cell 150 can be integral with shaft 106 or separate. The first pinching cell 150 can be connected to a first scaffolding section 110 and be configured to embed and grip, pinch, and/or "tweeze" the clot, as shown and described more particularly in FIGS. 2A-3B. As discussed herein, the term "tweeze" or "tweezing" is intended to refer to the sheathing of the pinching or squeezing cells (e.g., close cells of section 130 or cells 150 themselves) that causes respective struts to come together and tweeze or grip at least a portion of clot. In this respect, while the numbers of struts in a respective cell need not be limited, at least two strut surfaces must be included so as to tweeze corresponding clot material.

Shaft 106 can be a tapered wire shaft, and may be made of stainless steel, MP35N, Nitinol or other material of a suitably high modulus and tensile strength. Shaft 106 can also have indicator one or more bands proximal of the patient to indicate to the user when the distal end of the device 100 is approaching the end of the microcatheter during insertion.

Section 110 can include a collapsed configuration for delivery and an expanded configuration for clot retrieval, flow restoration and/or fragmentation protection. To move between the delivery to the expanded configurations, section 110 is configured to self-expand upon delivery from the microcatheter (e.g., release from the microcatheter) to a diameter larger than that of member 103. Section 110 can include an outer expandable body with an inner expandable member 103 with a generally tubular inner flow channel, to facilitate restoration of blood flow through clot immediately after the clot retrieval device 100 is deployed at an obstructive site. Expansion of the outer expandable body of section 110 can cause compression and/or displacement of the clot during expansion. The inner channel of member 103 may also comprise a portion that compresses an area of the clot in order to form a blood communication channel across the clot C. Such a channel can serve to reduce the pressure gradient across clot C, thus reducing one of the forces that must be overcome in order to retract the clot C. The flow channel of member 103 can also a flow path for oxygenated, nutrient carrying blood to reach the ischemic area distal of the clot.

The outer, expandable body of section 110 can provide a high level of scaffolding that provides an escape path or opening to urge the clot towards the opening or clot inlet 115. When inlet openings 115, in the outer expandable body of section 110 and/or between the outer expandable body and member 103, these inlet openings 115 provide the primary movement freedom available to the clot and so the expansion of section 110 urges the clot into a reception space defined between member 103, the outer expandable body and any clot scaffolding section(s) distal thereof. Inlet(s) 115 are configured to allow portions of the clot to enter the reception space between the respective outer expandable body of section 110 and member 103, and thus allow the clot to be retrieved without being excessively compressed.

This is advantageous because compression of clot causes it to dehydrate, which in turn increases the frictional properties of the clot, and increases its stiffness, all of which makes the clot more difficult to disengage and remove from the vessel. This compression can be avoided if the clot migrates inward through the outer wall of section 110 as the porous structure migrates outward towards the vessel wall. In some examples, the struts of sections 110, 120, and/or 130 include a relatively low coefficient of friction through polishing, hydrophilic coating, PTFE coating, silicon lubricant or the like so that the clot can easily slide off these segments and through corresponding inlet(s) 116 and into the reception space.

As shown, device 100 can include second scaffolding section 120 and third scaffolding section 130, each including outer expandable bodies similar structurally to that of section 110. However, an outer diameter of section 130 can be greater than an outer diameter of section 120, which can be greater than an outer diameter of section 110. Sections 110, 120, 130 are preferably made of a super-elastic or pseudo-elastic material (e.g., Nitinol or another such memory alloy with a high recoverable strain).

Device 100 is not so limited, however, and instead can be constructed from other material(s). In so selectively organizing and sizing sections 110, 120, 130, device 100 is configured to capture different clot types. In some examples, the outer diameter of section 130 can be sized as big as the diameter of vessel in which it is delivered to capture any fragments easily and avoid distal embolization. The outer diameter of section 120 can be relatively smaller while the outer diameter of section 110 can be even smaller to capture larger clots more easily (e.g., fibrin rich clots). Advantageously, the smaller diameter of section 110 can prevent blood vessel damage if the clot is fibrin rich and/or if it rolls over during retrieval. In some examples, section 110 can be beneficial in clot retention within device 100.

In some examples, varying diameters of sections 110, 120, 130 facilitates as described and shown can be particularly advantageous in capturing clot fragments during use that can be missed by section 110 since sections 120, 130 gradually increasing in diameter can securely capture fragments from the friable part of the clot. Sections 110, 120, 130 can be particularly advantageous in minimizing risk of damage to the vessel wall during clot retrieval. For example, if the clot is relatively large, the correspondingly small diameter of device 100 can allow space for the big clots and in turn minimize or reduce friction between the clot and the vessel wall during clot removal. Device 1 can also facilitate clot capture if the clot rolls over during use of device 100 or if the clot changes shape during retrieval.

Further, the outer diameters of section 110, 120, and 130 can otherwise vary and/or be substantially similar. For example, section 120 can include an inner member 103 while section 130 may not necessarily include any inner member 103 and instead include a substantially open distal end terminating in one or more distal crowns or apexes 136 not connected to any cell or element of section 130. Likewise, sections 110 and 120 can each include a substantially open distal end terminating in one or more distal crowns or apexes 116, 126, respectively, not connected to any cell or element of respective sections 110, 120.

Section 130 can be configured to include one or more struts configured to pinch clot C. In some examples, the pinch of section 130 can be achieved by forwarding a microcatheter or intermediate catheter over the device until a portion of clot is compressed between the tip of the catheter and a crown or strut of section 130 (e.g., apex 136). The diameter of section 130 can vary up to approximately 150% of the diameter of blood vessel BV at clot C. For example, the microcatheter can be forwarded distally to pinch a portion of the clot between the tip of the microcatheter and section 130 adjacent to the low radial force area. Section 130 distal of sections 110, 120 provides additional grip and control of the distal end of clot C during dislodgement and retention. Strut members and corresponding cells of section 130 can include a variety of shapes and designs configured for pinching fibrin rich clots, including those described in U.S. Pat. Nos. 10,292,723; 10,363,054; U.S. application Ser. No. 15/359,943; U.S. application Ser. No. 16/021,505; and U.S. application Ser. No. 16/330,703, each of which are incorporated by reference in their entirety as if set forth verbatim herein.

Compression of the clot by section 130 and/or the one or more cells 150 of this disclosure can alter the clot properties and make the clot less amenable to retrieval by making it firmer and "stickier" as described in WO2012/120490A, the entire contents of which are herein incorporated by reference. The device 100 of this disclosure is intended to facilitate clot retrieval by expanding between the clot and the vessel wall in such a way as to engage with the clot over a surface area and do so with minimal compression of the clot. In some examples, the pinch can be achieved by forwarding a microcatheter or intermediate catheter over the device until a portion of clot is compressed between the catheter and cell 150 or section 130. However, actuation of the respective cell 150 or section 130 is not so limited and can be also carried out by pulling one or more pull members attached therewith, by delivering a current to one or more of strut members of respective cell 150 or section 130 to cause to change from a collapsed configuration to pinch configuration, and/or the like. This pinch facilitates removal of the clot as it increases the grip of the device on the clot, particularly fibrin rich clots. It may also elongate the clot reducing the dislodgement force by pulling the clot away from the vessel wall during the dislodgement process.

The segmented and hinged design of cells 150 between sections 110, 120, 130 is also specifically tailored to achieving apposition in bends in the vasculature. The only connecting members of device 100 are cells 150 which function as hinge elements configured to self-align to the neutral axis and allow the device to easily articulate in the bend. In some examples, each of members 103 and cells 150 shown in FIG. 1 be laser cut from a single microtube having an outer diameter smaller than the inner diameter of the collapsed outer member when said outer member is loaded in a microcatheter. The opening angles of the cells of the inner tube are configured so that the change in length (or foreshortening) of the inner tube as it moves from the collapsed to expanded configuration is similar to that of the outer member, thus facilitating a connection between the distal ends of both inner and outer members.

A range of designs are envisaged for each of these elements as described throughout this document, and it is intended that any of these elements could be used in conjunction with any other element, although to avoid repetition they are not shown in every possible combination. Sections 110, 120, 130 are desirably made from a material capable of recovering its shape automatically once released from a highly strained delivery configuration. A superelastic material such as Nitinol or an alloy of similar properties is particularly suitable. The material could be in many forms such as wire or strip or sheet or tube. A particularly suitable manufacturing process is to laser cut a Nitinol tube and then heat set and electropolish the resultant structure to create a framework of struts and connecting elements. This framework can be any of huge range of shapes as disclosed herein and may be rendered visible under fluoroscopy through the addition of alloying elements (e.g., Platinum) or through a variety of other coatings or marker bands.

FIG. 2A depicts a close-up view of an example pinching cell 250, which is similar to cell 150 of device 100. Each of cells 250 can be configured embed and/or engage with and grip the clot to retain it securely for retraction. It is understood that each of the herein described pinching cells can be used interchangeably with clot retrieval devices as needed or required. Cell 250 can include a proximal end 204 and a distal end 208 between which strut members 212a, 212, 212c and 212d are positioned. One or more of strut members 212a, 212b, 212c and 212d can be configured as bowed or otherwise including tensioned flex so as to be capable of embedding in a clot and then being actuated by gripping or pinching the clot during use. Cells 250 can be actuated into the pinch configuration by being unsheathed from a sheath (e.g., a microcatheter), by being pulled or actuated by one or more pull members, delivering a current to one or more of strut members 212a, 212, 212c and 212d to cause at least a first portion of the one or more of strut members 212a, 212, 212c and 212d to change from a collapsed configuration to pinch configuration.

The diameter of cell 250 can range between approximately 2-10 millimeters depending on how much the design profile allows. One preferred diameter can be approximately 2.25 millimeters. In some examples, cells 250 can be small enough to fit in a 0.021 or 0.018 inch ID microcatheter.

FIG. 2B depicts a close-up view of another example pinching cell 250' with strut members 212a', 212b', and 212c' now shown with undulating edges. These undulations can be formed by being heat-set, crimped, or otherwise formed as needed or required. FIG. 2C depicts a close-up view of another example pinching cell 250" with strut members 212a", 212b", and 212c" each including one or more eyelets.

Figure 3A:
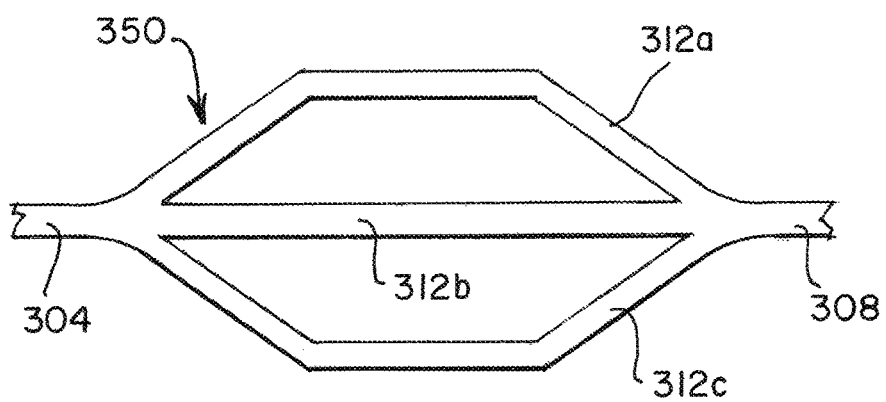
FIG. 3A depicts a close-up view of an example pinching cell.
Figure 3B:
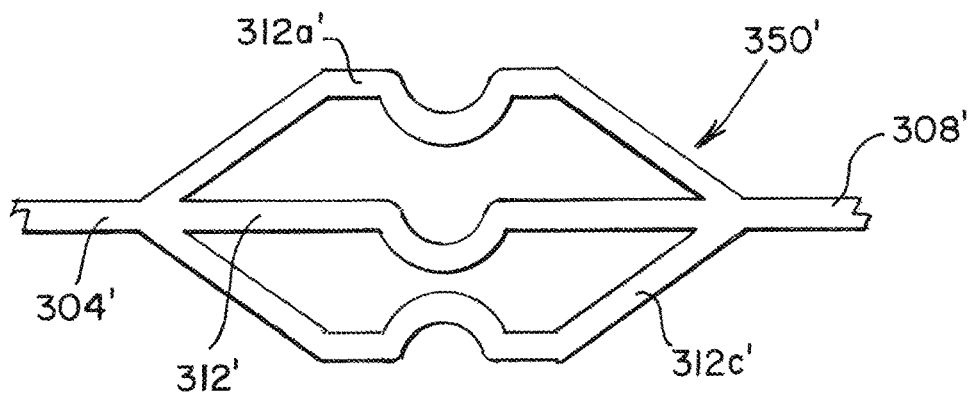
FIG. 3B depicts a close-up view of an example pinching cell.

FIG. 3B depicts a close-up view of another example pinching cell 350 with strut members 312a, 312b, and 312c now shown with relatively straight, non-curved strut members interconnected between ends 304, 308. These undulations can be formed by being heat-set, crimped, or otherwise formed as needed or required. FIG. 3C depicts a close-up view of another example pinching cell 350' with strut members 312a', 312b', and 312c' each including one or more notches or indentation.

Turning back to device 100, FIG. 4 depicts a side view of device 100 in an example blood vessel BV in use with an example clot C whereby device 100 is shown in the initial clot position engaged with clot C at section 110. Section 120 distal thereof is engaged as clot C can roll over and fragment, whereby fragments of clot C are shown captured by section 130. Device 100 of FIG. 4 also includes a first pinching cell 150 proximal of section 110, a second pinching cell 150 between sections 110, 120 and a third pinching cell 150 between sections 120, 130. Each cell 150 provides enhanced grip of the clot C, and any fragments thereof. Each of cells 150 can be particularly advantageous in capturing clots which may have fibrin core in the center, distal or proximal location in the clot C. Moreover, in use, if grip on some of a clot C is missed by one cell 150, one or more cells 150 distal thereof can engage and/or grip the clot C.

FIG. 5A depicts a side view of device 100 in blood vessel BV in use with clot C after the step shown in FIG. 4. As shown, clot C is engaged between and/or with sections 110, 120 so that device 100 is clearly configured to capture both fibrin rich and friable red blood cell rich clots. the overall device design will help to easily capture fibrin rich and red blood cell rich clots. The three pinch segments will help to capture a clot where the fibrin rich core may be located anywhere in the clot. The increasing diameter of the device will help to reduce clot fragmentation. Between sections 110, 120, cell 150 has also engaged clot C. In FIG. 5B, device 100 is sheathed by microcatheter 70 to cause cells 150 to grip and/or pinch the clot C tightly by pulling cells 150 inside the microcatheter 70 until resistance is felt, which would symbolize that the clot is gripped tightly within cells 150. Clot C can be secured by aspiration via microcatheter 70.

Figure 6A:
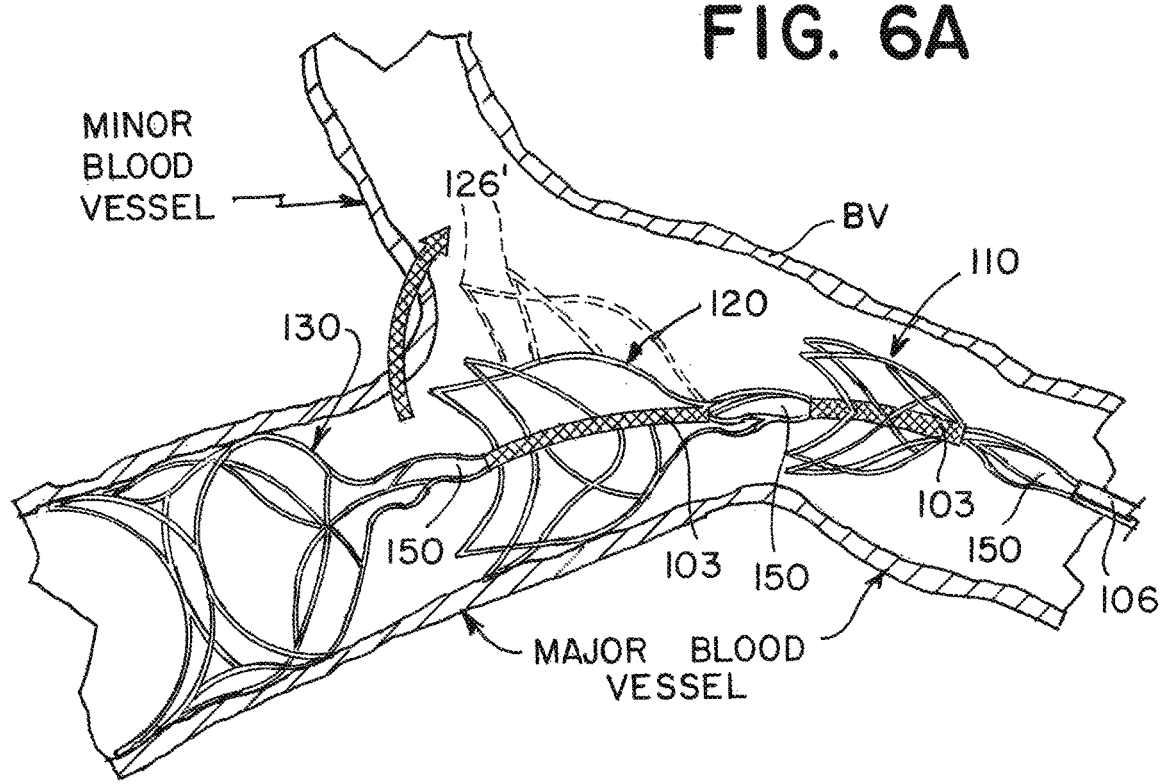
FIG. 6A depicts a side view of another example clot retrieval device in an example blood vessel in use with an example clot.
Figure 6B:
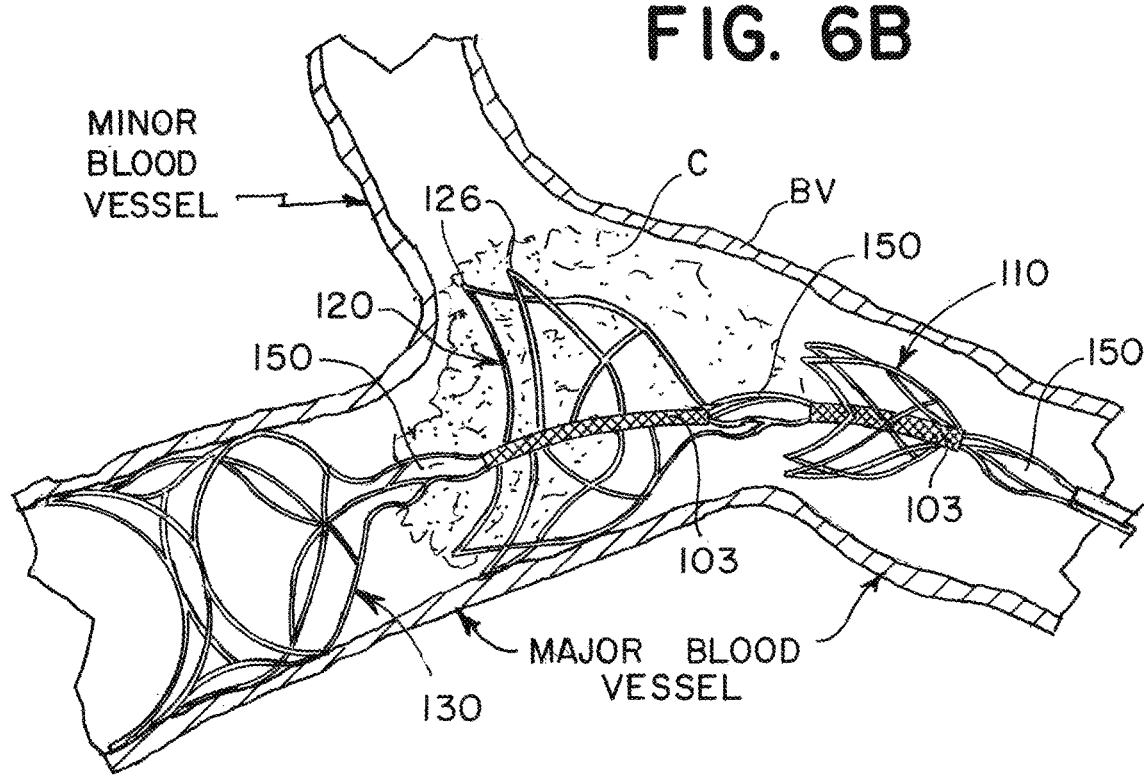
FIG. 6B depicts a side view of the example clot retrieval device of FIG. 6A in the example blood vessel in use with the example clot at the M1/M2 bifurcation.

FIG. 6A depicts a side view of device 100 in another example blood vessel BV with an example clot C. FIG. 6B depicts a side view of device 100 of FIG. 6A after actuation of a tilt feature associated with one or more distal crowns or apexes 116', 126'. Device 100 of FIGS. 6A-6B is particularly useful in capturing clots at vasculature bifurcations which are difficult to remove with one stentriever device of existing technologies. For purposes of this application, if a clot is present in two different branches of the blood vessel BV (e.g., M1 and M2), the blood vessel BV is referred as a "major blood vessel" and the other branches with the clot but no stentriever are referred to as "minor blood vessels." Through the tilt features of the one or more distal crowns or apexes 116', 126' of sections 110, 120, the outer cages are configured to open-up around bifurcations. When the one or more distal crowns or apexes 116', 126' of sections 110, 120 are angled as shown between FIGS. 6A-6B, the outer cage of each respective section 110, 120, can open up like a flower (e.g., by pivoting about one or more strut joints, junctions, or hinge elements as denoted in FIG. 6A with the large rotational arrow) and expand causing struts associated respective distal crowns or apexes 116', 126' in the bifurcations to capture clot.

Moreover, these tilt features of the one or more distal crowns or apexes 116', 126' of sections 110, 120 can cause an increase in outer diameter of sections 110, 120 that enhances grip of the clot C even at the bifurcation as the clot C is gripped between the inner and the outer cages of sections 110, 120. When the clot is present at the bifurcation, the three pinch features can facilitate clot grip and/or pinch in each different branches of the blood vessels. The gradual increasing diameter of the outer cage between sections 110, 120, 130 and respective inner segments (e.g., member 103, cells 150, etc.) can keep the clot C retained inside the vessel BV. Re-sheathing of device 100 with microcatheter 70, as well as aspiration therethrough, can also enhance device 100's grip of the clot C present at the bifurcations.

Turning to FIG. 7A, device 100' is shown, which is similar to device 100. Device 100' includes five (5) sequentially positioned hinge elements, pinching cells 150, including at least one with sections 110 and 120. Outer diameters of sections 110, 120, and 130, similar to device 100, generally increase from smallest at section 110 to largest at section 130. Although not shown, an inner body 103 with corresponding flow channel may be included with at least one of sections 110, 120, similar to device 100. Arranging cells 150 as shown can ease manufacturing as well as enhance gripping the clot via the additional cells 150. Increasing diameter between sections 110, 120, and 130 can prevent clot fragmentation.

Turning to FIG. 7B, device 100" is shown, which is similar to device 100' with the main difference being all three sections 110", 120", 130" have approximately the same diameters. Either of devices 100, 100', and 100" from a single tube for of a memory alloy (e.g., Nitinol) as to the inner segment (e.g., cells 150, inner body 103, etc.) and a single tube of memory alloy can similarly be used to manufacture the outer tube corresponding to sections 110, 120, 130. In some examples, relatively small gaps can be provided between sections 110, 120 and cells 150 to create a clot inlet mouth and expose cells 150 to the clot(s).

Figure 8:
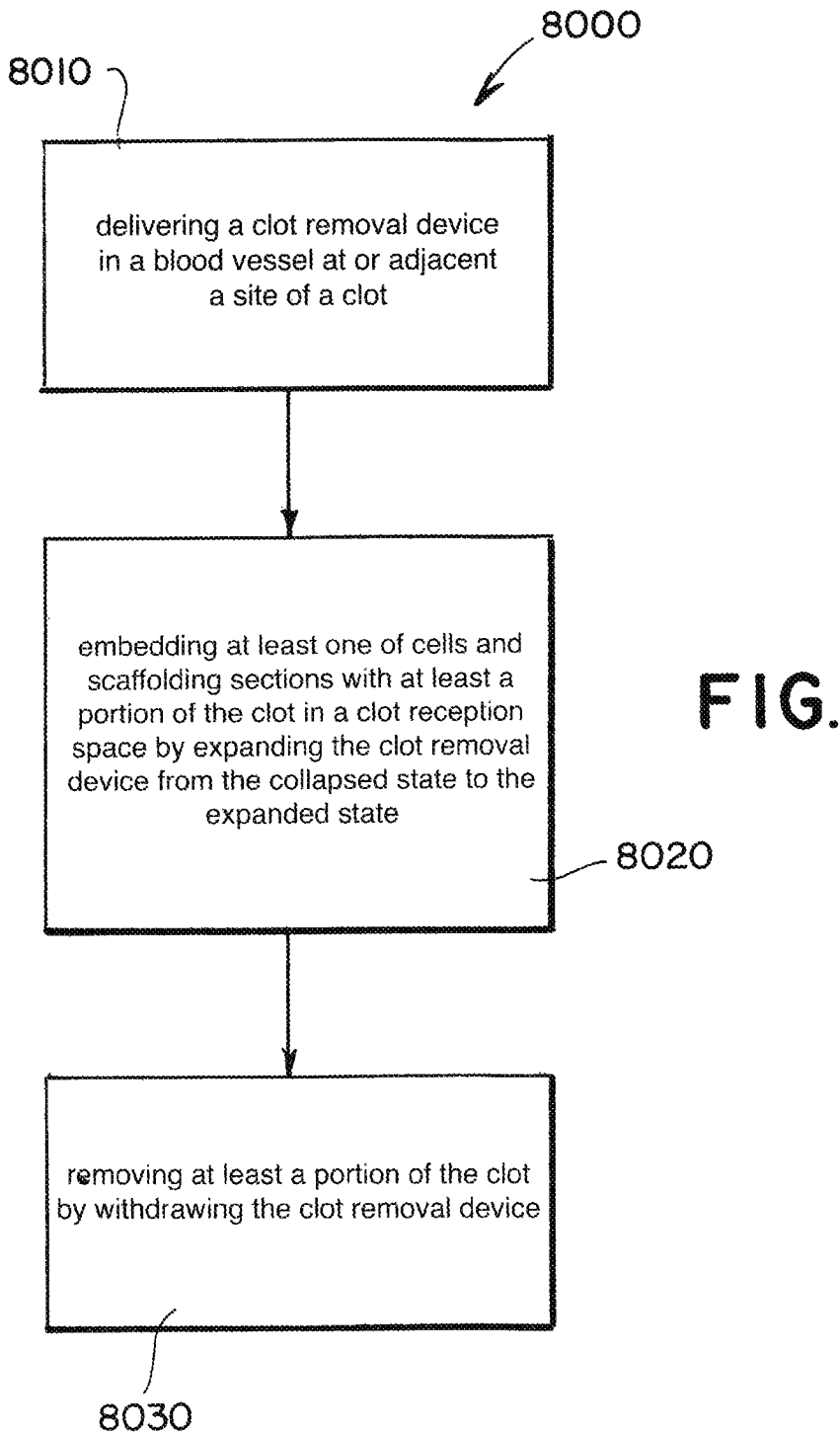
FIG. 8 is a flow diagram illustrating a method of removing a clot from a blood vessel of a patient, according to aspects of the present disclosure.

FIG. 8 is a flow diagram illustrating a method of removing a clot from a blood vessel of a patient, according to aspects of the present disclosure. The method steps in FIG. 8 can be implemented by any of the example means described herein or by similar means, as will be appreciated. Referring to method 8000 as outlined in FIG. 8, in step 8010, delivering a clot removal device in a blood vessel at or adjacent a site of a clot, the clot removal device comprising a collapsed state and an expanded state and including a first scaffolding section, a second scaffolding section distal of the first scaffolding section by a first hinged element comprising a pinching cell comprising a collapsed state and an expanded state configured to pinch at least a portion of a clot, and a third scaffolding section distal of the second scaffolding section by a second hinged strut element comprising a pinching cell comprising a collapsed state and an expanded state configured to pinch at least a portion of the clot. In step 8020, method 8000 includes embedding at least one of cells and scaffolding sections with at least a portion of the clot in a clot reception space by expanding the clot removal device from the collapsed state to the expanded state. In step 8030, method 8000 includes removing at least a portion of the clot by withdrawing the clot removal device. Method 8000 can end after step 8030. In other embodiments, additional steps according to the examples described above can be performed.

The disclosure is not limited to the examples described, which can be varied in construction and detail. The terms "distal" and "proximal" are used throughout the preceding description and are meant to refer to a positions and directions relative to a treating physician. As such, "distal" or "distally" refer to a position distant to or a direction away from the physician. Similarly, "proximal" or "proximally" refer to a position near to or a direction towards the physician.

In describing examples, terminology is resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method can be performed in a different order than those described herein without departing from the scope of the disclosed technology. Similarly, it is also to be understood that the mention of one or more components in a device or system does not preclude the presence of additional components or intervening components between those components expressly identified.

As discussed herein, a "patient" or "subject" can be a human or any animal. It should be appreciated that an animal can be a variety of any applicable type, including, but not limited to, mammal, veterinarian animal, livestock animal or pet-type animal, etc. As an example, the animal can be a laboratory animal specifically selected to have certain characteristics similar to a human (e.g., rat, dog, pig, monkey, or the like).

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It must also be noted that, as used in the specification and the appended claims, the singular forms "a," "an," and "the" include plural referents unless the context clearly dictates otherwise. Ranges can be expressed herein as from "about" or "approximately" one particular value and/or to "about" or "approximately" another particular value. When such a range is expressed, other exemplary embodiments include from the one particular value and/or to the other particular value.

The descriptions contained herein are examples of the disclosure and are not intended in any way to limit the scope of the disclosure. While particular examples of the present disclosure are described, various modifications to devices and methods can be made without departing from the scope and spirit of the disclosure. For example, while the examples described herein refer to particular components, the disclosure includes other examples utilizing various combinations of components to achieve a described functionality, utilizing alternative materials to achieve a described functionality, combining components from the various examples, combining components from the various example with known components, etc. The disclosure contemplates substitutions of component parts illustrated herein with other well-known and commercially-available products. To those having ordinary skill in the art to which this disclosure relates, these modifications are often apparent and are intended to be within the scope of the claims which follow.

What is claimed is:

1. A clot removal device, comprising:
a first scaffolding section comprising a first pinching cell;
a second scaffolding section distal of the first scaffolding section and directly connected to the first scaffolding section by a first hinged element comprising a second pinching cell comprising three or more strut members, wherein at least two of the three or more strut members of the second pinching cell comprise at least one eyelet element configurable in a collapsed state or an expanded state to pinch at least a portion of a clot;
a third scaffolding section distal of the second scaffolding section and directly connected to the second scaffolding section by a second hinged element comprising a third pinching cell comprising a collapsed state and an expanded state configured to pinch the at least a portion of the clot, wherein at least two of three or more strut members of the third pinching cell comprises at least one eyelet element configurable in a collapsed state or an expanded state to pinch the at least a portion of the clot; and
an outer diameter of the third scaffolding section being greater than an outer diameter of the second scaffolding section which is greater than an outer diameter of the first scaffolding section;
wherein the first hinged element has a proximal end and a distal end between which the second pinching cell is positioned, each of the at least two of the three or more strut members of the second pinching cell comprises the at least one eyelet element configurable in the collapsed state or the expanded state to pinch the at least a portion of the clot, wherein the proximal end of the first hinged element comprises a single proximal strut connected to the first scaffolding segment section and the distal end of the first hinged element comprises a single distal strut connected to the second scaffolding segment section, each of the at least two of the three or more strut members of the second pinching cell has a proximal end connected to the single proximal strut, each of the at least two of the three or more strut members of the second pinching cell has a distal end connected to the single distal strut; each of the at least two of the three or more strut members of the second pinching cell is comprised of a single strut, each of the single struts has the at least one eyelet disposed thereon spaced from and between the strut proximal end and the strut distal end.

2. The clot removal device of claim 1, further comprising: a hinged element comprising a pinching cell proximal of the first scaffolding section and connected to a distal end of a shaft.

3. The clot removal device of claim 2, wherein at least one of three or more strut members of the first pinching cell further comprise a sinusoidal or notched strut pattern.

4. The clot removal device of claim 1, the first scaffolding section extended at least partially over an inner body comprising a flow channel configured to engage the clot and restore blood flow through the clot, the inner body comprising a collapsed state and an expanded state;
the outer diameters of the first scaffolding section and second scaffolding section being greater than an outer diameter of the inner body in the expanded state to define a clot reception space between the inner body and the separate first and second scaffolding sections, the device further comprising:
a first clot inlet mouth between the first and second scaffolding section.

5. The clot removal device of claim 4, each hinged element configured to self-align the corresponding scaffolding sections to articulate in bends of the vasculature, the second scaffolding section extended at least partially over an inner body comprising a flow channel configured to engage the clot and restore blood flow through the clot, the inner body of the second scaffolding section comprising a collapsed state and an expanded state;
each hinged element being the only point of contact between respective clot scaffolding sections.

6. The clot removal device of claim 5, a proximal end of each respective flow channel joined at a respective proximal end of a respective scaffolding section and a distal end of each respective flow channel joined at a respective a subsequent scaffolding section.

7. The clot removal device of claim 4, each of the first, second, and third scaffolding sections comprising an open distal end,
each of the first, second, and third scaffolding sections comprise a plurality struts formed of closed cells, the distal end of at least one of the first, second, and third scaffolding sections terminates in at least one distal apex free from connection to an adjacent closed cell of the respective scaffolding sections.

8. The clot removal device of claim 7, the at least one distal apex being a petal or leaf member configured to open up in a flower-like manner and expand in one or more bifurcations of the vasculature to remove the clot.

9. The clot removal device of claim 4, each of the first, second, and third scaffolding sections comprising an open distal end, each of the first, second, and third scaffolding sections comprise a plurality struts formed of closed cells, the distal end of at least one of the first, second, and third scaffolding sections terminating in crowns with no distal connecting elements, at least one of the crowns configured to pivot open in a flower-like manner as clot engages therewith.

10. The clot removal device of claim 4, wherein the device is configured so that expanding the clot removal device causes at least one of the pinching cells, the first scaffolding section, the second scaffolding section, and the third scaffolding section to deform the at least a portion of the clot.

11. The clot removal device of claim 1, a ratio of a diameter of each pinching cell between the collapsed state and a clot pinching state of the expanded state is from approximately 1.5:1 to 4:1.

12. The clot removal device of claim 1, the third scaffolding section comprising a constrained delivery configuration and an at least partially constrained clot pinching configuration, at least a portion of the third scaffolding section being configured to engage the clot in the expanded state and to pinch the clot on movement from the expanded state to the clot pinching configuration.

13. The clot removal device of claim 12, the third scaffolding section comprises a clot pinching structure configured to pinch the clot on movement from the expanded state to the clot pinching configuration.

14. The clot removal device of claim 1, the third scaffolding section being configured to exert an outward radial force when deployed within a lumen whose inner diameter is lower than that of the expanded state, the outward radial force varying in a generally sinusoidal pattern along a length of the third scaffolding section, the generally sinusoidal pattern comprising a wave pattern and the amplitude generally consistent along the length.

15. The clot removal device of claim 1, at least five (5) pinching cells being positioned end-to-end between proximal and distal ends of the device.

16. The clot removal device of claim 1, wherein the second hinged element has a proximal end and a distal end between which the third pinching cell is positioned, each of the at least two of the three or more strut members of the third pinching cell comprises the at least one eyelet element configurable in the collapsed state or the expanded state to pinch the at least a portion of the clot, wherein the proximal end of the second hinged element comprises a single proximal strut connected to the second scaffolding segment and the distal end of the second hinged element comprises a single distal strut connected to the third scaffolding segment, each of the at least two of the three or more strut members of the third pinching cell has a proximal end connected to the single proximal strut, each of the at least two of the three or more strut members of the third pinching cell has a distal end connected to the single distal strut; each of the at least two of the three or more strut members of the third pinching cell is comprised of a single strut, each of the single struts has the at least one eyelet disposed thereon spaced from and between the strut proximal end and the strut distal end, the at least one eyelet having a first curved portion and a second curved portion, each of the first curved portion and the second curved portion having a proximal end and a distal end, the proximal end of the first curved portion is connected to the proximal end of the second curved portion and the distal end of the first curved portion is connected to the distal end of the second curved portion.

17. The clot removal device of claim 1, wherein the at least one eyelet of each of the at least two of the three strut members of the second pinching cell has a first curved portion and a second curved portion, each of the first curved portion and the second curved portion having a proximal end and a distal end, the proximal end of the first curved portion is connected to the proximal end of the second curved portion and the distal end of the first curved portion is connected to the distal end of the second curved portion.

\* \* \* \* \*